US007002001B2

(12) United States Patent
Farries et al.

(10) Patent No.: US 7,002,001 B2
(45) Date of Patent: Feb. 21, 2006

(54) DOWN-REGULATION RESISTANT C3 CONVERTASE

(75) Inventors: Timothy Charles Farries, Cambridge (GB); Richard Alexander Harrison, Cambridge (GB)

(73) Assignee: Imutran Limited, Cambridge (GB)

( * ) Notice: Subject to any disclaimer, the term of this patent is extended or adjusted under 35 U.S.C. 154(b) by 245 days.

(21) Appl. No.: 09/875,519

(22) Filed: Jun. 6, 2001

(65) Prior Publication Data

US 2002/0068059 A1 Jun. 6, 2002

Related U.S. Application Data

(62) Division of application No. 09/142,334, filed as application No. PCT/GB97/00603 on Mar. 4, 1997, now Pat. No. 6,268,485.

(30) Foreign Application Priority Data

| | | |
|---|---|---|
| Mar. 7, 1996 | (GB) | 9604865 |
| Jun. 7, 1996 | (GB) | 9611896 |
| Jul. 8, 1996 | (GB) | 9614293 |
| Nov. 19, 1996 | (GB) | 9624028 |

(51) Int. Cl.
*C07H 21/04* (2006.01)

(52) U.S. Cl. .................................................. 536/23.5
(58) Field of Classification Search .............. 530/311.7; 424/94.63, 178.1; 435/212; 514/12, 515; 536/23.5
See application file for complete search history.

(56) References Cited

U.S. PATENT DOCUMENTS

| | | | |
|---|---|---|---|
| 4,661,347 | A | 4/1987 | Muller-Eberhard et al. |
| 5,849,297 | A | 12/1998 | Harrison et al. |

FOREIGN PATENT DOCUMENTS

| | | |
|---|---|---|
| WO | 96 07738 | 3/1996 |

OTHER PUBLICATIONS

Ngo et al., (V), newly cited, in The Protein Folding Problem and Tertiary Structure Prediction, 1994, Merz et al., (ed.), Birkhauser, Boston, MA, pp. 433 and 492–495.*
Farries et al Xenotransplantation (1998) 5:29–34.*
McNearney, TA, J. Exp. Med. (1987) 166:1525–35.
Nicol, PAE (1973) Immunol.24:259–275.
Pangburn, MK (1984) Springer Semin. Immunopathol. 7: 163–92.
Kotwal, GJ Nature (1988)335 (6186): 176–8.
Lambris et al., Biochem. J. vol. 217, pp. 323–326 (1984).
Fritzinger et al., Proc. Natl. Acad. Sci. USA, vol. 91, pp. 12775–12779 (1994).
O'Keefe et al., J. Biol. Chem., vol. 263, No. 25, pp. 12690–12697 (1988).
Hohler et al., Hum Genet. No. 96, pp. 539–541 (1995).
Lambris et al., J. Immunol. vol. 151, No. 11, pp. 6123–6134 (1993).
Ekdahl et al., J. Immunol., vol. 144, No. 11, pp. 4269–4274 (1990).
Fritzinger et al., J. Immunol., vol. 149, No. 11, pp. 3554–3562 (1992).
Daoudaki et al., J. Immunol., vol. 140, No. 5, pp. 1577–1580 (1988).
Watanabe et al., Mol. Immunol. 30, Supplement 1, p. 62 (1993).
Kew R.R. et al., J. Clin. Invest. 75: pp. 1000–1007 (1985).
Isenman D. E. et al., Biochemistry 20: pp. 4458–4467 (1981).
Fishelson Z. et al., J. Immunol. 132(3): pp. 1430–1434 (1984).
Taniguchi–Sidle A., Journal of Immunology, vol. 153, pp. 5285–5302 (1994).
Pangburn M.K., J. Immunol. vol. 142(8), pp. 2759–2765 (1989).
Fries L.F., et al., Database Biosis, pp. 1640–1655 (1984) (J. Exp. Med. vol. 160(6) Abstract only.
Becherer, J.D. & Lambris, JD, 1988, J. Biol. Chem. 263:14586–91.
Becherer, J.D., et al., 1992, Biochemistry 31:1787–94.
Ganu, VS & Muller–Eberhard, HJ, 1985, Complement 2:27.
Lambris, JD et al., 1985, Proc. Natl. Acad. Sci. USA 82:4235–9.
Lambris JD et al., 1988, J. Biol. Chem. 263:12147–50.
Esparza, I., et al., 1991, Eur. J. Immunol. 21:2829–38.
Davis, A.E., et al., 1984, J. Immunol. 132:1960–5.
Ekdahl, K.N., et al., 1990, J. Immunol. 144:4269–74.
Taniguchi–Sidle A., et al., The Journal of Biological Chemistry, vol. 267, No. 1, pp. 635–643 (1992).
Taniguchi–Sidle et al., Mol. Immunol. vol. 30, p. 54 (1993).
Fishelson Z., Molecular Immunology, vol. 28, No. 4/5, pp. 545–552 (1991).

* cited by examiner

*Primary Examiner*—Christina Chan
*Assistant Examiner*—F. Pierre Vandervegt
(74) *Attorney, Agent, or Firm*—Susan Hess

(57) ABSTRACT

Native complement pathway proteins modified such that the protein is capable of forming a down-regulation resistant C3 convertase. Preferably the modified protein is a modified human C3 protein. DNA sequences encoding such proteins are also provided, together with DNA constructs. Conjugates comprising such proteins and a specific binding moiety, for example an antibody, are also described, as are uses of such proteins and/or conjugates in therapy.

1 Claim, 19 Drawing Sheets

FIG. 1(I)

Figure 3:
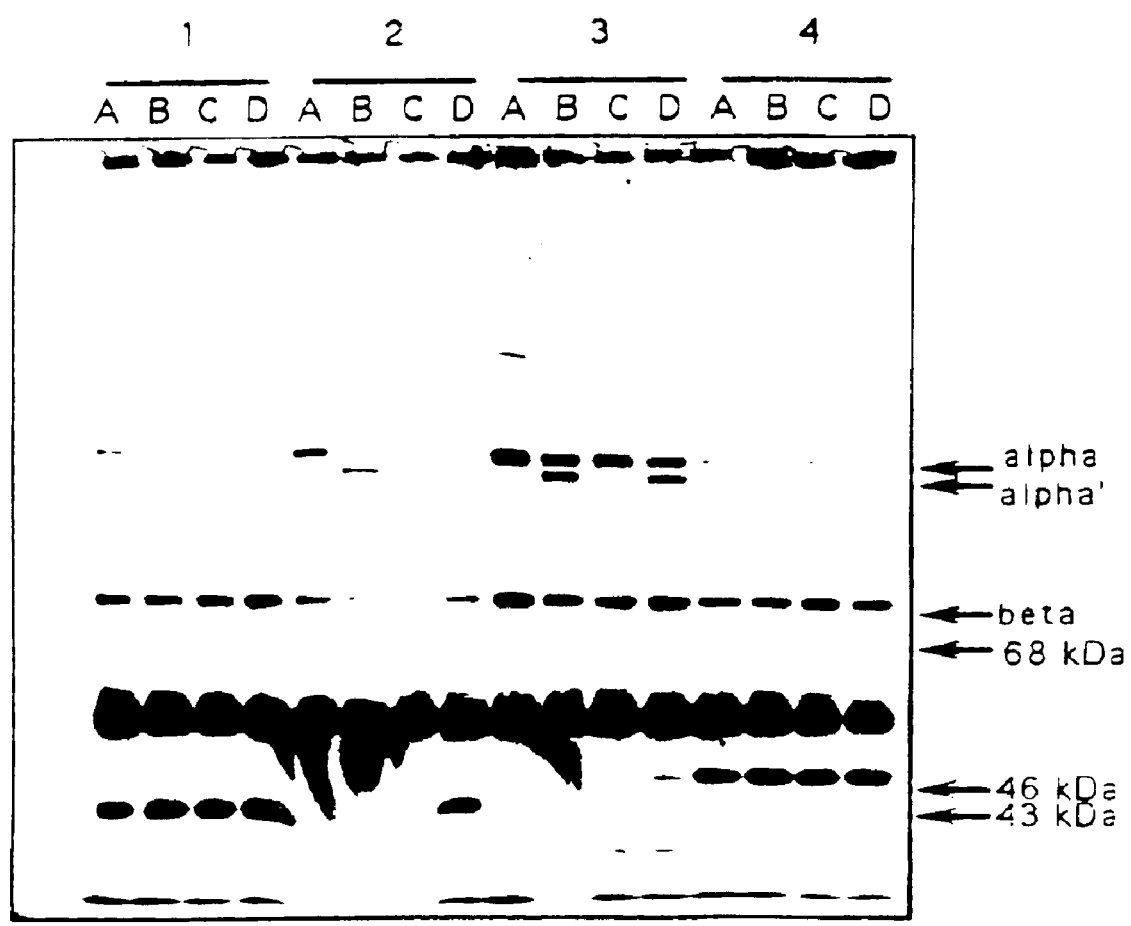

```
         10          20          30          40          50          60
MGPTSGPSLL LLLLTHLPLA LGSPHYSIIT PNILRIESEE THVLEAHDAQ GDVPVTVTVH 70          80          90         100         110         120
DFPGKKLVLS SEKTVLTFAT NHMGNVTFTI PANREFKSEK GRNKFVTVQA TFGTQVVEKV 130         140         150         160         170         180
VLVSLQSGYL FIQTDKTIYT PGSTVLYRIF TVNHKLLFVG RTVMVNIENP EGIPVKQDSL 190         200         210         220         230         240
SSQNGLGVLP LSWDIPELVN MGQWKIRAYY ENSPQQVFST EFEVKEYVLP SFEVIVEPTE 250         260         270         280         290         300
KFYYIYNEKG LEVTITARFL YGKKVEGTAF VIFSIQDGEQ RISLFESLKR IPIEDGSGEV 310         320         330         340         350         360
VLSRKVLLEG VQNPRAEDLV GKSLYVSATV ILHSGSDMVQ AERSGIPIVT SPYQIHFTKT 370         380         390         400         410         420
PKYFKPGMPF DLMVFVTNPD GSPAYRVFVA VQGEDTVQSL TQGDGVAKLS INTHPSQKPL 430         440         450         460         470         480
SITVRTKKQE LSEAEQATRT MQALPYSTVG NSNNYLHLSV LRTELAPGET LNVNFLLRMD 490         500         510         520         530         540
RAHEAKIRYY TYLIMNKGRL LKAGRQVREP GQDLVVLPLS ITTDFIPSFR LVAYYTLIGA 550         560         570         580         590         600
SGOREVVADS VWVDVKDSCV GSLVVKSGQS EDRQPVPGQQ MTLKIEGDHG ARVVLVAVDK 610         620         630         640         650         660
GVFVLNKKNK LTQSKIWDVV EKADIGCTFG SGKDYAGVFS DAGLTFTSSS GGQTAQRAEL 670         680         690         700         710         720
QCPQPAARRR RSVQLTEKRM DKVGKYPKEL RKCCEDGMRE NPMRFSCQRF CPFISLGEAC 730         740         750         760         770         780
KKVFLDCGNY ITELRRQHAR ASHLGLARSM LDEDIIAEEN IVSRSEFPES WLWNVEDLKE 790         800         810         820         830         840
PPKNGISTKL MNIFLKDGIT TWEILAVSHS DKKGICVADP FEVTVMQDFF IDLRLPYSVV 850         860         870         880         890         900
RNECVEIRAV LYNYRQNQEL KVRVELLHNP AFCSLATTKR RHQQTITIPP KSSLSVPYVI 910         920         930         940         950         960
VPLMTGLQEY EVKAAVYHHF ISDGVRKSLK VVFEGIRMNK TVAVRTLDFE RLGREGVQKE 970         980         990        1000        1010        1020
DIFPADLSDC VPDTESETRI LLQGTFVAQM TEDAVDAERL KHLIVTFSGG GEQNMIGMTP 1030        1040        1050        1060        1070        1080
TVIAVHYLEE TEQWEKFGLE KRQGALELIK KGYTQCLAFP QFSSAFAAFV KRAPSTWLTA 1090        1100        1110        1120        1130        1140
YVVFTSLAV NLIAIDSGVL GGAVKWLLLE KQKFDGVTGE DAFVTHQEMI GGLRNNNEKD 1150        1160        1170        1180        1190        1200
HALTAFVLLS LDEAHEICEE QVNSLFGSIT KAGDFLERNY HILQRSYTVA IAGYALAQMG
```

```
        1210       1220       1230       1240       1250       1260
    RLKGFLLNKF LTTAKDKNRW EDPGKQLYNV EATSYALLAL LCLKDFDFVP PVVRWLNEQR 1270       1280       1290       1300       1310       1320
    YYGGGYGSTC ATFMVFQALA QYQKDAPDHQ ELNLDVSLCL PSRSSKITHR IHWESASLLR 1330       1340       1350       1360       1370       1380
    SEETKENEGF TVTAEGKGCC TLSVVTMYHA KAKDQLTCIK FDLKVTIKPA PETEKRPQDA 1390       1400       1410       1420       1430       1440
    KNTMILEICT RYRGDCDATM SILDISMMTG FAPDTDCLKC LANGVDRYIS KYELDKAFSD 1450       1460       1470       1480       1490       1500
    RNTLIIYLDK VSHSEDDCLA FKVHQYFWVE LIQPGAVKVY AYYNLEESCT RFYHPEREDG 1510       1520       1530       1540       1550       1560
    KLNKLCRDEL CRCAEENCFI QKSDDKVTLE ERLDKACEPG VDYVYKTRLV KVQLSNDFDE 1570       1580       1590       1600       1610       1620
    YIMAIECTIK SGSDEVQVGQ QRTFISPIKC REALKLEEKK HYLMWGLSSD FWGEXPNLSY 1630       1640       1650       1660
    IIGKDTWVEH WPEEDECQDE ENQKQCQCLG AFTESMVVFG CPN
```

FIG. 1(II)

FIG. 2(I)

```
          cctctccct  ctgtccctct  gtccctctga  ccctgcactg  tccsagcaec
          12         20          30          40          50         60 atgggaccca cctcaggtcc cagcctgctg ctcctgctac taacccacct cccctggct
70         80         90         100         110         120 ctgtggagtc ccatgtactc tatcatcacc cccaacatct tgcggctgga gagcgaggag
130        140        150        160         170         180 accatggtgc tggaggccca cgacgcgcaa ggggatgttc cagtcactgt tactgtccac
190        200        210        220         230         240 gacttcccag gcaaaaaact agtgctgtcc agtgagaaga ctgtgctgac ccctgccacc
250        260        270        280         290         300 aaccacatgt gcaacgtcac cttcacgatc ccagccaaca gggagttcaa gtcagaaaag
310        320        330        340         350         360 gggttcaaca agttcgtgac cgtgcaggcc accttcgggs cccaagtggt ggagaaggtg
370        380        390        400         410         420 gtgctggtca gcctgcagag cgggtacctc ttcatccaga cagacaagac catctacacc
430        440        450        460         470         480 cctggctcca cagttctcta tcggatcttc accgtcaacc acaagctgct acccgtgggc
490        500        510        520         530         540 cggacggtca tggtcaacat tgagaacccg gaaggcatcc cggtcaagca ggactccttg
550        560        570        580         590         600 tcttctcaga accagcttgg cgtcttgccc ttgtcttggg acattccgga actcgtcaac
610        620        630        640         650         660 atgggccagt ggaagatccg agcctactat gaaaactcac cacagcaggt cttctccact
670        680        690        700         710         720 gagtttgagg tgaaggagta cgtgctgccc agtttcgagg tcatagtgga gcctacagag
730        740        750        760         770         780 aaatctact acatctataa cgagaagggc ctggaggtca ccatcaccgc caggttcctc
790        800        810        820         830         840 tacggaaaga aagtggaggg aactgccttc gtcatcttcg ggatccagga tggcgaacag
850        860        870        880         890         900 aggatttccc tgcctgaatc cctcaagcgc attccgattg aggatggctc ggggsaggtt
910        920        930        940         950         960 gtcctgagcc ggaaggtact gctggacggc gtgcagaacc cccagcaga agacctggtg
970        980        990        1000        1010        1020 gggaagtctt tgtacgtgtc tgccaccgtc atcttgcact caggcagtga catggtgcag
1030       1040       1050        1060        1070        1080 gcagagcgca gcggatccc catcgtgacc tctccctacc agatccactc caccaagaca
1090       1100       1110        1120        1130        1140 cccagtacct tcaaaccagg aatgcccttt gacctcatgg tgttcgtgac gaaccctgat
1150       1160       1170        1180        1190        1200 cggtccccag cctaccgagt ccccgtggca gtccagggcc aggacactgt gcagtctcta
1210       1220       1230        1240        1250        1260
```

FIG. 2(II)

```
acccagggag atggcgtggc caaactcagc atcaacacac accccagcca gaagcccttg
   1270       1280       1290       1300       1310       1320 agcatcacgg tgcgcacgaa gaagcaggag ctctcggagg cagagcaggc taccaggacc
   1330       1340       1350       1360       1370       1380 atgcaggctc tgccctacac caccgtgggc aactccaaca attacctgca tctctcagtg
   1390       1400       1410       1420       1430       1440 ctacgtacag agctcagacc cggggagacc ctcaacgtca acttcctcct gcgaatggac
   1450       1460       1470       1480       1490       1500 cgcgcccacg aggccaagat ccgctactac acctacctga tcatgaacaa gggcaggctg
   1510       1520       1530       1540       1550       1560 ctgaaggccg gacgccaggt gcgagagccc ggccaggacc tggtggtgct gccccctgcc
   1570       1580       1590       1600       1610       1620 atcaccaccg acttcatccc ttccttccgc ctggtggcgt actacacgct gatcggtgcc
   1630       1640       1650       1660       1670       1680 agcggccaga gggaggtggt ggccgactcc gtgtgggtgg acgtcaagga ctcctgcgtg
   1690       1700       1710       1720       1730       1740 ggctcgctgg tggtaaaaag cggccagtca gaagaccggc agcctgtacc tgggcagcag
   1750       1760       1770       1780       1790       1800 atgaccctga agatagaggg tgaccacggg gcccgggtgg tactggtggc cgtggacaag
   1810       1820       1830       1840       1850       1860 ggcgtgttcg tgctgaacaa gaagaacaaa ctgacgcaga gtaagatctg ggacgtggtg
   1870       1880       1890       1900       1910       1920 gagaaggcag acatcggctg caccccgggc agtgggaagg attacgccgg tgtcttctcc
   1930       1940       1950       1960       1970       1980 gacgcagggc tgaccttcac gagcagcagt ggccagcaga ccgcccagag ggcagaactt
   1990       2000       2010       2020       2030       2040 cagtgcccgc agccagccgc ccgccgacgc cgttccgtgc agctcacgga gaagcgaatg
   2050       2060       2070       2080       2090       2100 gacaaagtcg gcaagtaccc caaggagctc cgcaagtgct gcgaggacgg catgcgggag
   2110       2120       2130       2140       2150       2160 aaccccatga ggttctcgtg ccagcgccgg acccgtttca tctccctggg cgaggcgtgc
   2170       2180       2190       2200       2210       2220 aagaaggtct tcctggactc ctgcaactac atcacagagc tgcggcggca gcacgcgcgg
   2230       2240       2250       2260       2270       2280 gccagccacc tgccctggc caggactaac ctgatgagg acatcattgc agaagagaac
   2290       2300       2310       2320       2330       2340 atcgtttccc gaagtgagtt cccagagacc tggctgtgca acgttgagga cttgaaagag
   2350       2360       2370       2380       2390       2400 ccaccgaaaa atggaatccc tacgaagctc atgaatatat ttttgaaaga ctccatcacc
   2410       2420       2430       2440       2450       2460 acgtggaga ttctggctct gagcatgtcg gacaagaaag ggatctgtct ggcagacccc
   2470       2480       2490       2500       2510       2520 ctcgagctca cactaatcca ggacttcttc atccacctgc ggctacccta tcctgtttctt
   2530       2540       2550       2560       2570       2580
```

FIG. 2(III)

FIG. 2(IV)

```
caataccaaa aggacgcccc tgaccaccag gaactgaacc ttgatgtgtc cctccaactg
     3910      3920      3930      3940      3950      3960 cccagccgca gctccaagat caccaccgt atccactggg aatctgccag cctcctgcga
     3970      3980      3990      4000      4010      4020 tcagaagaga ccaaggaaaa tgagggtttc acagtcacac ctgaaggaaa aggccaaggc
     4030      4040      4050      4060      4070      4080 accttgtcgg tggtgacaat gtaccatgct aaggccaaag atcaactcac ctgtaataaa
     4090      4100      4110      4120      4130      4140 ttcgacctca aggtcaccat aaaaccagca ccgaaacag aaagaggcc tcaggatgcc
     4150      4160      4170      4180      4190      4200 aagaacacta tgatccttga gatctgtacc aggtaccggg gagaccagga tgccactatg
     4210      4220      4230      4240      4250      4260 tctatattgg acatatccat gatgactggc tttgctccag acacagatga cctgaagcag
     4270      4280      4290      4300      4310      4320 ctggccaatg gtgttgacag atacatctcc aagtatgagc tggacaaagc cttctccgat
     4330      4340      4350      4360      4370      4380 aggaacaccc tcatcatcta cctggacaag gtctcacact ctgaggatga ctgtctagct
     4390      4400      4410      4420      4430      4440 ttcaaagttc accaatactt taatgtagag cttatccagc ctggagcagt caaggtctac
     4450      4460      4470      4480      4490      4500 gcctattaca acctggagga aacctgtacc cggttctacc atccggaaaa ggaggatgga
     4510      4520      4530      4540      4550      4560 aagctgaaca agctctgccg tgatgaactg tgccgctgtg ctgaggagaa ttgcttcata
     4570      4580      4590      4600      4610      4620 caaaagtcgg atgacaaggt cacccctggaa gaacggctgg acaaggcctg tgagccagga
     4630      4640      4650      4660      4670      4680 gtggactatg tgtacaagac ccgactggtc aaggttcagc tgtccaatga ctttacgag
     4690      4700      4710      4720      4730      4740 tacatcatgg ccattgagca gaccatcaag tcagcctcgg atgaggtgca gttggacag
     4750      4760      4770      4780      4790      4800 cagccacgt tcatcagccc catcaagtgc agagaagccc tgaagctgga ggagaagaaa
     4810      4820      4830      4840      4850      4860 cactacctca cgtgggtct ctcctccgat ttctgggag agaagccag cctcagctac
     4870      4880      4890      4900      4910      4920 atcatcggga aggacacttg ggtggagcac tggcctgagg agcacgatct ccaagacgaa
     4930      4940      4950      4960      4970      4980 gagaaccaga aacaatgcca ggaccttct gccttcaccg agagcatggt tgtctttggg
     4990      5000      5010      5020      5030      5040 tgccccaact gaccacacc ccattcc
     5050      5060
```

DOWN-REGULATION RESISTANT C3 CONVERTASE

This is a division of U.S. application Ser. No. 09/142,334, filed Apr. 15, 1998, now U.S. Pat. No. 6,268,485 which is a 371 of International Application No. PCT/GB 97/00603, filed Mar. 4, 1997.

The present invention relates to novel modified proteins capable of forming C3 convertases resistant to down-regulation, DNA sequences encoding such proteins and the use of such proteins as therapeutic agents, particularly for use in depleting levels of complement pathway proteins or in targeting complement attack (C3b deposition) at specific sites.

The complement system functions in the immune response of humans and other vertebrates, being of major importance in the effector functions such as phagocytosis, cytolysis and recruitment of cells that induce local inflammatory responses [15]. These properties are desirable for elimination of invading pathogens, such as bacteria, but undesirable when triggered to act against host tissues (e.g. in post-ischemic reperfusion injury [3]) or against foreign therapeutic material (e.g. hyperacute rejection of xenografts [7]). There have been attempts to abrogate these undesirable properties by exploiting derivatives of complement regulatory proteins whose normal function is to suppress complement activation [10, 18].

The complement system comprises proteins both on the surface of cells, (receptors and regulators) as well as in the fluid-phase (blood plasma and other extracellular environments). The critical step for the generation of responses is the proteolytic conversion of C3 to the fragments C3b and C3a. C3a is an anaphylatoxin that, like C5a, attracts mast cells to the site of challenge, resulting in local release of histamine, vasodilation and other inflammatory effects. The nascent C3b has an ability to bind to surfaces around its site of generation. This C3b then focuses attack by the cytolytic complement components (C5–C9).

Surface-bound C3b, and its degradation products, also function as ligands for C3 receptors mediating, for example, phagocytosis [15]. There are two distinct pathways of complement activation that both result in conversion of C3 to C3b and subsequent responses. The classical pathway is commonly triggered by complexes of antibody with antigen, initiating an enzyme cascade involving the proteins C1q, C1r, C1s, C2 and C4. The alternative pathway depends on an activation loop involving C3 itself and requiring factors B and D.

Conversion of C3 to C3b (or C3i) produces a product that can combine with factor B, giving C3bB (or C3iB). These complexes are acted upon by factor D to generate C3bBb, which is a C3 convertase capable of cleaving more C3 to C3b, leading to more C3bBb and even more C3 conversion. Under certain circumstances the C3bBb complex is stabilised by association with the positive regulator properdin (P). However, this positive-feedback loop is normally limited to a slow tick-over by regulatory proteins, notably factor H and factor I.

Factor H (and structurally related cell-associated molecules) (i) displaces B and Bb from C3b, and (ii) acts as a cofactor for factor I which cleaves C3b into iC3b thereby preventing any recombination with factor B to form more C3 convertases. The pathway is "fired" into amplified generation of C3b in the presence of surfaces, such as many bacterial cell walls, that bind nascent C3b and impede its regulation by factors H and I. Nascent C3b is also able to bind to endogenous cells. Endogenous cell surfaces normally exposed to complement are therefore additionally protected by membrane-bound regulators such as MCP, DAF and CR1 acting in a similar manner to factor H.

There are a few rare naturally occurring conditions where the normal fluid-phase regulation cannot occur and spontaneous C3 conversion ultimately results in generalised depletion of C3 from the circulation:—(i) genetic deficiencies of factor H or I [13], (ii) the presence of antibodies (nephritic factors) that bind to C3bBb and impede dissociation [4], and (iii) contact with a protein in cobra venom, called cobra venom factor (CVF), that combines with factor B and forms a C3 convertase enzyme which does not contain C3b and is not affected by factors H and I [14]. These illustrate the normal physiological importance of down-regulation of complement in the absence of specific activation.

There are also circumstances where specific activation occurs, but is unwanted, particularly when it is directed against issues of the host (e.g. tissue damaged by ischemia or surgery) or against foreign material deliberately given for therapeutic purposes (such as a xenograft, artificial organ or a dialysis membrane). The complement activation results in undesirable attack and further damage, so in these cases it would be beneficial to block or inhibit the activation and response.

Existing approaches to preventing complement-mediated damage have targeted the use of down-regulatory proteins (CR1, MCP, DAF and factors H and I) to inhibit complement activation. Complement inhibitors like factor I, factor H and soluble derivatives of the membrane-bound proteins CR1, DAF, MCP do suppress the fluid-phase amplification loop of the alternative pathway. Therefore there have been attempts to use these molecules, particularly CR1 (which seems to be the most potent) to reduce complement-mediated damage in models of physiological situations [10, 18].

Factor H is endogenously present in blood plasma in high concentrations (typically 0.3–0.5 mg/ml [15]), so even though increased levels of inhibitors do dampen-down fluid-phase reactions, their potency is weak so large amounts of purified proteins would have to be administered in vivo (e.g probably in excess of 5 mg/Kg body weight of soluble CR1). In addition, the alternative pathway is activated by surfaces where the effect of factor H is already impeded. While this does not necessarily concomitantly reduce the activities of other inhibitors, the same factors suggest that they are unlikely to be completely or universally effective.

Cobra Venom Factor(CVF) has the property of generating a stable C3 convertase which can be used experimentally to deplete complement in animals in vivo, and in other samples (e.g. human blood plasma) in vitro. CVF is potent (e.g. 40 $\mu$g/Kg can destroy the complement activity of a mouse [16]). However, there are disadvantages that make it unsuitable for therapeutic use in humans.

Firstly, it is obtained from cobra venom (a difficult source to obtain and dangerous to handle) and must therefore be carefully purified from the venom neurotoxins. There is also the obvious difficulty in obtaining supplies. This problem cannot readily be overcome by cloning and expressing the gene ex vivo, because there are post-translational modifications that occur in the snake (specific proteolytic processing) that may be difficult (or impossible) to reproduce n vitro. In addition, the enzymes and digestion conditions required for this processing are currently unknown. Secondly, the protein is of foreign origin (to humans) and therefore immunogenic. This precludes its repeated therapeutic use, as would be required to decomplement a patient over many weeks (e.g. to allow xenograft survival).

Although CVF has some structural and functional homologies with human C3 [17], it also has major differences in both respects (e.g. chain structure, site of biosynthesis, insensitivity to complement regulators, formation of a stable C3 convertase). It is not derived from the cobra equivalent of C3 which is known, having been cloned and sequenced, and which in gross structure and function resembles human C3 more closely than does CVF [8].

CVF is a venom-specific product of an animal of great evolutionary distance from homo sapiens. It is therefore not practicable to use genetic manipulation to modify this protein into a product that can be used non-immunogenically in humans.

We have now devised an alternative strategy which relies on by-passing the physiological regulation and, instead of inhibiting complement activation, causes the system to be super-activated. This has two applications. Firstly, it can be used in vivo to activate complement until one or more components are exhausted, resulting in loss of ability to produce local responses to any subsequent challenge (such as a xenograft). Secondly, the unregulated super-activation can be deliberately localised to a particular target (e.g. a virus or a virally-infected cell) to increase the sensitivity of that target to complement-mediated destructive responses.

The term "regulators of complement activation" is used herein to include all proteins that act to inhibit amplification of C3 conversion, and is not intended to be resticted in meaning to those proteins whose genes are located in the RCA genetic locus. It does not however include "up-regulators" such as properdin. "C3 conversion" is defined as the proteolytic conversion of C3 into C3b and C3a, unless otherwise indicated, and "C3 convertase" (or simply "convertase") is defined as an enzyme (typically a complex of two or more protein components; for example C3bBb, C3iBb, CVFBb or C4b2a) that catalyses this reaction.

Thus, in a first aspect the invention provides a native complement pathway protein modified such that the protein is capable of forming a down-regulation resistant C3 convertase.

By "native" is meant naturally occurring, ie is obtainable in nature. Thus, the definition encompasses any naturally occurring complement pathway protein modified as defined above. It is not intended to be restricted to species specific proteins. In other words, a modified human protein could be used as a down-regulation resistant C3 convertase in other mammalian species, for example. Typically, modified complement pathway proteins from the same species will be used.

Modification of the C3 DNA coding sequence, for example using site directed mutagenesis, can produce a variant of C3 that is resistant to complement regulatory proteins while retaining positive functional properties (cleavage to C3b by C3 convertase) and features of structural integrity (correct chain structure, and presence of a thiolester bond). The invention described herein relates to genetically-modified forms of native complement proteins, for example human C3, whose C3b fragment acquires the property of being resistant to physiological complement regulation. Because of this resistance, these molecules can generate stabilised forms of the corresponding C3 convertase that produce amplified conversion of C3 to C3b, and later degradation products, in physiological environments (e.g. in vivo).

In a preferred embodiment the invention provides a modified human C3 protein which is resistant to cleavage by factor I.

This can be achieved by modifying residues of the protein at proteolytic sites.

A particularly preferred embodiment of the invention relates to a modified human C3 protein wherein the protein is modified by replacement of either Arg-1303, Arg-1320 so both by another amino acid. The other amino acid may be Tyrosine, Cystine, Tryptophan, Glutamine, Glutamic acid or Glycine. Arg-1303 is preferably replaced by Glutamic acid or Glycine (less preferably by Glutamine). Arg-1320 is preferably replaced by Glutamine.

Other stategies for producing suitable modified proteins of the invention include:

i) Reduced susceptibility to the inhibitory actions of factor H and related proteins (eg. MCP, DAF, CR1). For example, in human C3 residues 767–776 and 1209–1271 have been implicated in factor H binding [20, 24], and substitution of one or more of these residues or other residues also associated with the action of these proteins, could reduce the binding of one or more of these regulatory proteins.

ii) Reduced rate of dissociation of C3bBb. Mutations can be introduced which would strengthen the interaction between C3b and Bb. This would result in both a reduction in spontaneous decomposition of the enzyme, and diminish the effectiveness of factor H (and related regulators) in displacing Bb from C3b.

These mutations are desirable to reduce the rates of both the spontaneous and the factor H-mediated decomposition of C3bBb. Even in the absence of factor H, the fluid phase C3bBb complex has a half-life of only about 10 mins at 37° C. in the presence of properdin [6].

iii) Human C3 residues 752–761 are implicated in binding factor B. It is a highly conserved region in C3, and a closely related sequence is found in C4. As C4 binds the factor B homolog C2, the strong similarity of this region between C3 and C4, together with its high conservation in C3, further supports its role in C3 as a factor B binding site. Thus, changes in this region could have effects on B affinity and on the stability of C3bBb.

iv) Resistance to other regulators of complement activation such as CR1, DAF and MCP would also be desirable. The mode of action of these regulators are all similar to factor H, so additional mutagenesis would not necessarily be required. Similarly, some pathogenic organisms express their own inhibitors of complement activation that are often structurally and functionally homologous to factor H (e.g. Vaccinia virus secretory peptide [ ]). These molecules protect the invaders against immune responses, and it would be advantageous to be able to attack them with targeted C3 convertase enzymes resistant to these defences.

v) Mutations that increase the stabilisation of the C3 convertase by properdin. The activity of properdin is to stabilise the C3bBb complex, retarding spontaneous and factor H-decendent dissociation. This stabilisation is ineffective in the fluid-phase, but seems to be more important in amplifying the process once it has already started on a suitable activating surface [5]. Increasing its activity (by increasing its affinity) may upset the balance in the fluid-chase, and thereby promote spontaneous C3 conversion. This should be particularly useful in combination with the other modifications described above.

vi) Mutations that prevent the C3bBb from possessing C5 convertase activity. When used to deplete active C3 from the circulation an undesirable side-effect could be the generation of large amounts of anaphylactic peptides. The most potent of these is C5a, which is cleaved from C5 by some C3 convertase enzymes. This reaction probably depends on the affinity of the convertase for another molecule of C3b [11], and so may be subject to suppression by mutations to the C3 that remove this interaction.

vii) Improved activity of the C3 convertase. The active site of the C3bBb C3 convertase enzyme resides in the Bb portion. The C3b component presumably functions to impose an active conformation on Bb and/or to bind and orientate the substrate to be acted upon by Bb. This is not known, but in either case there may be scope for enhancing the activity of the convertase through mutations in C3.

viii) Expression in a functional form. Wild-type C3 requires conversion to C3b before it can combine into a new C3 convertase complex. When used in vivo, a requirement for conversion to C3b (or C3i) would delay the action of the modified C3. It would therefore be desirable to either administer the protein in a form capable of immediate convertase formation, or to administer pre-formed convertase complexes. It is therefore advantageous to generate a functionally C3b-like reagent ex-vivo. This could be achieved in vitro (e.g. by proteolysis).

ix) Modifications to the native protein which serve to introduce new cleavage sites such that peptide regions required for factor B binding are retained but those required exclusively for factor H binding can be specifically removed. For example, sites can be introduced such that the C3b-like form of the modified C3 can be further cleaved into a form that still binds factor B but is less susceptible to inactivation by factors H and I.

x) Modifications in other regions which may affect the C3b interaction with factor B and/or factor H.

The invention is based on reversing the traditional approach by promoting C3 conversion to deplete C3 and thereby disable the system. An additional application of the invention is the potential to promote C3 conversion at a particular site, and thereby recruit the complement-dependent effector mechanisms to attack a specific target.

Therefore the ultimate effect will be to increase the amount of C3 conversion when the modified protein is administered into a physiological medium (e.g. blood) containing regulators of complement activation. This activity can then be used either to deplete that medium of native C3, or to localise the C3 conversion at a desired target.

The analogue of C3 whose C3b-fragment is resistant to the actions of factor I (e.g. the derivative described in example 1) would bind factor B, which would then be cleaved by factor D and eventually dissociate in an inactive form. In the absence of inactivation by factor I, the modified C3b would be able to repeatedly bind new molecules of factor B and thereby promote its inactivation. Therefore another potential application of modifications described in this invention would be the inactivation of the alternative pathway by consumption of factor B activity. An analogous approach could also be used to modify C4 to promote the consumption of C2, and thereby disable the classical pathway of complement activation.

The invention includes any other protease used in an analogous manner to the C3bBb enzyme which leads to cleavage of C3 to C3b, despite the presence of regulators of complement activation.

The invention also includes DNA sequences which code for a protein of the invention as well as DNA constructs comprising such DNA sequences.

"DNA sequences" include all other nucleic acid sequences which, by virtue of the degeneracy of genetic code, also code for the given amino acid sequence or which are substantially homologous to this sequence. These sequences are thus also included within the scope of the invention.

Nucleic acid sequences which are "substantially homologous" are also within the scope of the present invention.

"Substantial homology" may be assessed either at the nucleic acid level or at the amino acid level. At the nucleic acid level, sequences having substantial homology may be regarded as those which hybridise to the nucleic acid sequences of the invention under stringent conditions (for example, at 35 to 65° C. in a salt solution of about 0.9M). At the amino acid level, a protein sequence may be regarded as substantially homologous to another protein sequence if a significant number of the constituent amino acids exhibit homology. At least 55%, 60%, 70%, 80%, 90%, 95% or even 99%, in increasing order of preference, of the amino acids may be homologous.

As discussed above the proteins of the invention can be used to achieve localised complement activation effects. One way of ensuring this is to conjugate the protein to a moiety which will bind at the desired target. Thus, in another aspect the invention provides a conjugate comprising a protein of the invention linked to a specific binding moiety, for example a specific binding protein. An example of such a protein would be an antibody or an antigen binding fragment thereof.

The proteins of the invention are intended to be administered to a subject to elicit a desired therapeutic effect. To that end therefore the invention also provides:

a) A protein of the invention for use in therapy;

b) The use of a protein or a conjugate of the invention in the manufacture of a medicament for use in depleting levels of complement pathway protein, and in particular for use in preventing rejection of foreign matter;

c) A Pharmaceutical formulation comprising one or more proteins or conjugates of the invention together with one or more pharmaceutically acceptable carriers—and/or excipients; and d) A method of reducing complement pathway protein in a mammal which comprises administering to the mammal a protein of the invention, preferably in the form of a pharmaceutical formulation.

Pharmaceutical formulations may be presented in unit dose forms containing a predetermined amount of active ingredient per dose. Such a unit may contain as a minimum, for example, 1 mg of active ingredient, and preferably 2–3 mg. The upper limit which such a unit dose can contain will depend on many factors such as the condition being treated, the route of administration and the age, weight and condition of the patient as well as economic considerations. As an example a unit dose form can contain as much as 10 mg or even 100 mg of active ingredient.

The proteins of the invention could be used in vivo to disable the complement system. Circumstances where this may be desirable include the following:

(a) In order to prevent complement-mediated destruction or damage to a transplant, particularly a xenograft (material transplanted from a different species of animal), and especially a discordant xenograft (where the donor and recipient species are discordantly related). The recipient would be decomplemented prior to the operation and maintained in this state until the transplant had either been accommodated or been replaced by a more compatible organ.

The initial treatment could be made within several days before transplantation. Additional decomplementation could be required at times of rejection crisis. The treatments may be accompanied by the use of anti-histamine reagents to control the general inflammatory responses (e.g. vasodilation) likely to result from the generation of C3a and/or C5a.

Decomplementation may also be beneficial in the use of artificial organs or tissues (e.g. artificial kidney dialysis membranes) which activate the complement system. As described above, the protein may be given either as the unactivated form, a functionally C3b-like form or a preformed active C3 convertase (like C3bBb). These may be administered by any route whereby the active convertase will encounter the circulating C3 (e.g. intravenously, subcutaneously etc.).

Another alternative would be an ex vivo treatment, for example by transfusing the circulation through a matrix bearing the active convertase. This could have the advantage of allowing anaphylactic peptides (C3a and C5a) and other low molecular weight inflammatory mediators (e.g. histamine and nitric oxide) to be removed (e.g. by dialysis) prior to the decomplemented blood (or plasma) being returned to the patient.

(b) To prevent complement-mediated damage resulting from major surgery. The patient would be decomplemented, as above, preferably before the operation (but if necessary afterwards) and kept in this state until the danger of additional internal injury due to complement-dependent immune attack had diminished.

(c) To minimise complement-mediated damage resulting from non-surgical injury. In these cases the decomplementation must be performed after the initial injury, but the formulations and methods of administration are likely to be otherwise similar to those described above. This may be particularly useful when the recovery involves reperfusion of an ischemic tissue by the circulation (e.g. myocardial ischemia, frostbite, burns etc.).

(d) To minimise complement-mediated damage resulting from antibody-antigen interactions. Complement-mediated defensive responses are particularly undesirable in autoimmune diseases which may include glomerulonephritis, haemolytic anaemia, myasthenia gravis, Diabetes type I, rheumatoid arthritis and multiple sclerosis. Disabling the complement system during severe episodes of disease may alleviate the condition, for instance by local administration to the joint in rheumatoid arthritis.

(e) To make a specific pathogenic target more susceptible to complement-mediated immune mechanisms. In this approach, the aim is not to use the super-active C3 convertase to produce generalised depletion of C3, but instead to use the convertase locally to concentrate the C3 conversion at a desired target. The target may be a pathogenic organism, such as a bacteria, virus or other parasite, or a deleterious host cell or tissue, such as a tumour cell or a virally-infected cell. The C3 convertase could be localised to the target either by local administration (e.g. direct injection, possibly in a medium that retards its dispersion into the general circulation), or by combining with a targeting moiety, e.g. an antibody. Thus the modified protein could be linked to a specific immunoglobulin either by chemical cross-linking of the proteins, or by joining the DNA coding sequences and expressing (and purifying) the fusion protein (e.g. in the case of IgG, either the heavy or the light chain could be attached to C3 and co-expressed with C3, or both chains could be combined within one complete fusion polypeptide), or by incorporation of specific coding sequences (eg. for "leucine zipper"-like domains) to the DNA of both fusion partners (eg. modified C3 and specific antibody) such that the expressed products, when mixed together, self-associate to form stable conjugates. The fusion protein could then be administered locally or into the general circulation.

Liposomes (bearing the antibody on the surface with the modified protein either on the surface or inside the liposome) and/or virions (e.g. engineered to express the proteins on their surface) could also be used for co-delivery of antibody and modified protein. This strategy could be used directly, alone or in combination with other treatments, at any stage in the disease process. It may be particularly appropriate for use in eliminating any cancerous cells left in the circulation after surgical removal of a tumour. The antibody-modified protein conjugates could also be used ex vivo to eliminate pathogenic tissue. For example to kill leukaemic cells from an extracted bone-marrow and then returning the remaining healthy cells to the patient.

Alternatively lymphocytes that do not match the MHC types of the recipient could be eliminated from a bone marrow prior to transplantation. Also the modified protein could be linked to an antigen, and this combination could be used, either in vivo or ex vivo, to attack lymohocytes of undesirable reactivities (e.g. against transplant or self tissue).

The same technology would be applicable to treating other species, using either a human modified protein derivative, or a similar analogue tailor-made for that species.

Preferred features of each aspect of the invention are as for each each other aspect mutatis mutandis.

The invention will now be described by way of the following examples, which should not be construed as in any way limiting the invention. The examples refer to the accompanying drawings in which:

FIG. 1: shows the predicted protein sequence of human C3 as encoded in PC3;

(using the standard one letter amino acid code)

FIG. 2: shows the cDNA sequence in PC3;

(using the standard one letter deoxynucleotide code for the sense strand, written 5'-3').

FIG. 3: shows a visualisation of modified proteins of the invention.

Figure 4:
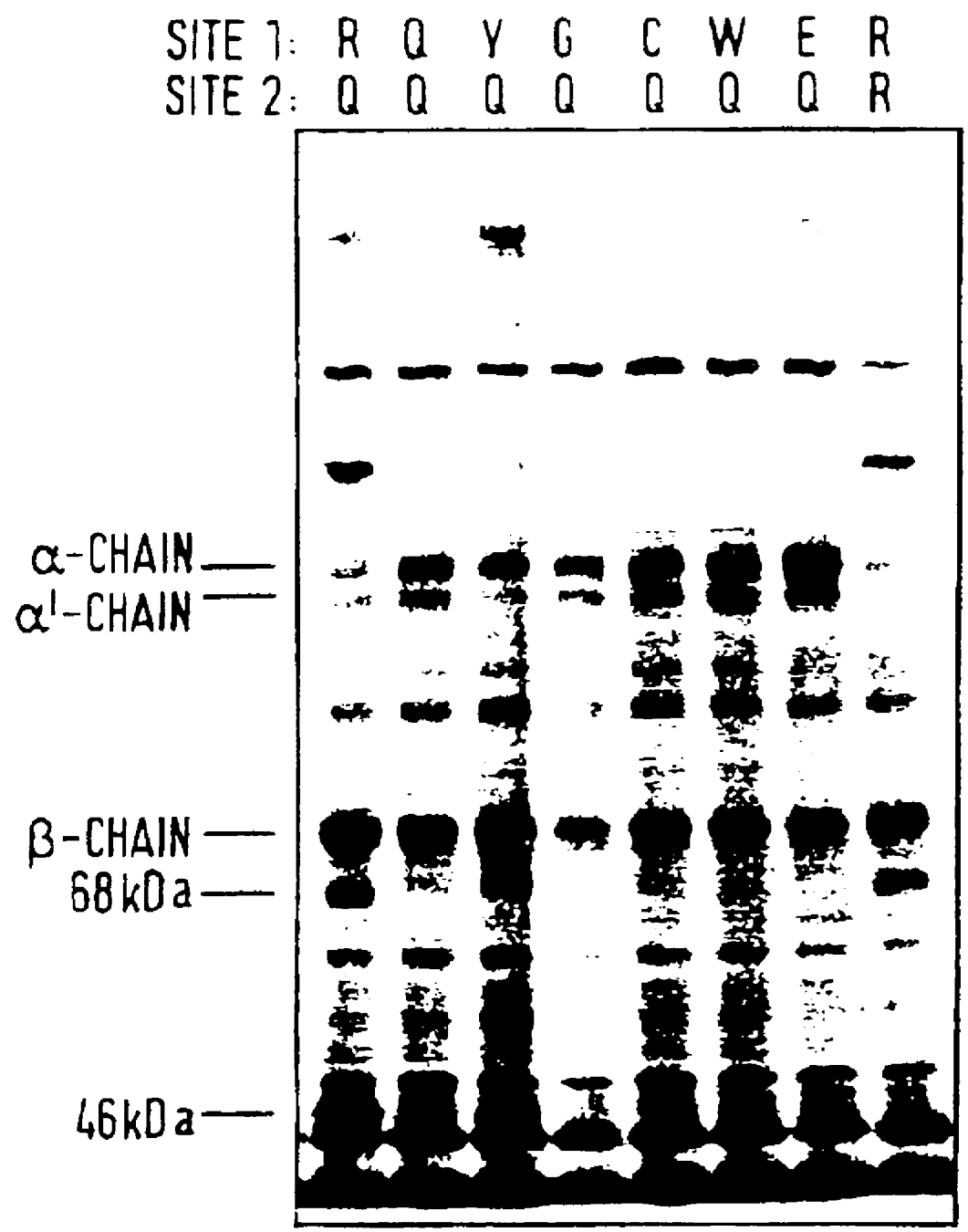

FIG. 4: shows the effect of various mutations to human C3 which replace Arg 1303 or Arg 1320 on factor I-medicated cleavage at these sites. N.B.

1. [35S]-biosynthetically labelled samples.
2. Reactions performed at normal ionic strength.
3. Immunoprecipitated with anti-C3.
4. SDS-PAGE under reducing conditions.
5. Autoradiography.

Figure 5:
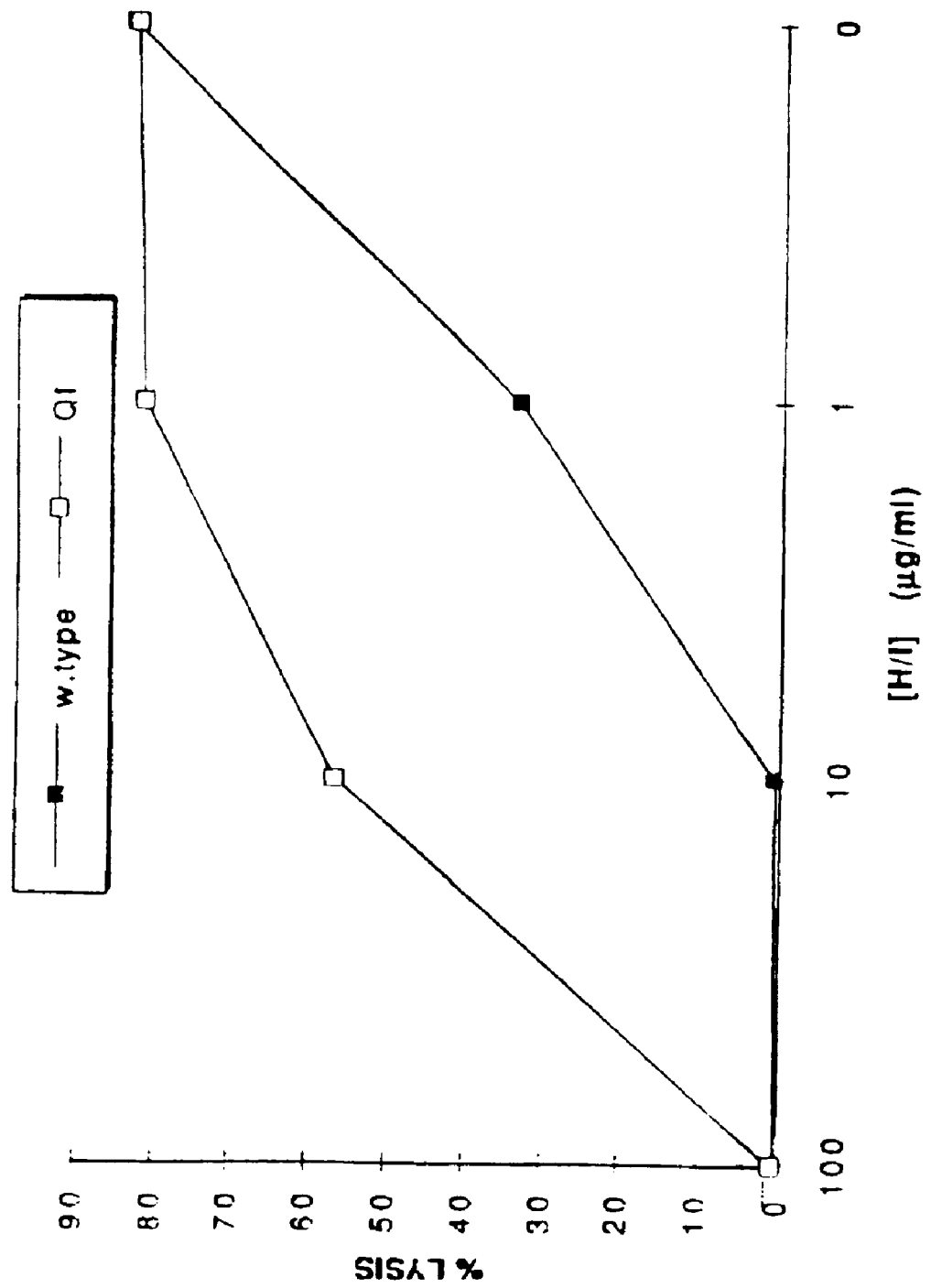

FIG. 5: shows enhanced resistance of human C3 incorporating the Arg 1303->Gln 1303 mutation to inactivation by factors I and H.

Figure 6:
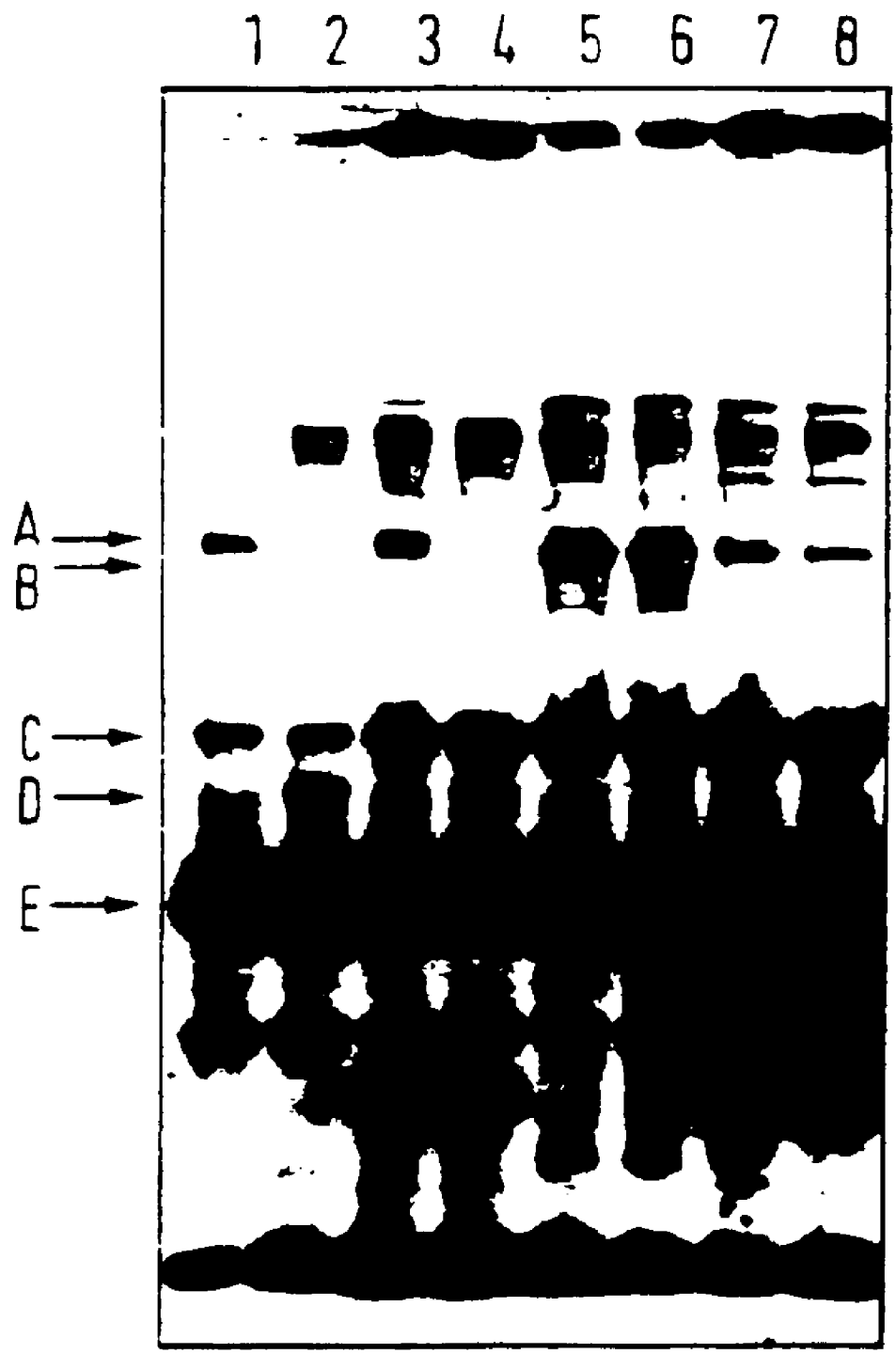

FIG. 6: shows an analysis of the cleavage of a C3 convertase mutated at amino acid residues 752–754 and 758–760.

This is a photograph of a Western Blot developed from a 7.5% polyacrylamide SDS-PAGE gel (reducing conditions), after electrophoretic transfer onto nitrocellulose, probing with a sheen anti-human C3 antibody, and development with horse-radish-peroxidase-coupled anti-sheep Immunoglobulin antibody and Enhance ChemiLuminescence (method and detection reagents from Amersham, U.K.) recorded on X-ray film. The cleavage reactions and detection procedure were performed as described in Example 4 with reference to the results shown in FIG. 3.

Key:

Tracks 1–4: wild-type C3 (expressed in COS cells)

Tracks 5–8: Mutant C3 (residues 752–754 changed to Gly-Ser-Gly and residues 758–760 also being changed to Gly-Ser-Gly) (expressed in COS cells)

Tracks 1,5: no addition

Tracks 2,6: _+CVFBb

Tracks 3,7: +factors H+I

Tracks 4,8: +CVFBb+factors H+I
The bands indicated by arrows are:

A: C3 alpha-chain

B: C3 alpha'-chain

C: C3 beta chain

D: 68 kDa cleavage product of C3 alpha'-chain

E: IgG heavy chain

Figure 7:
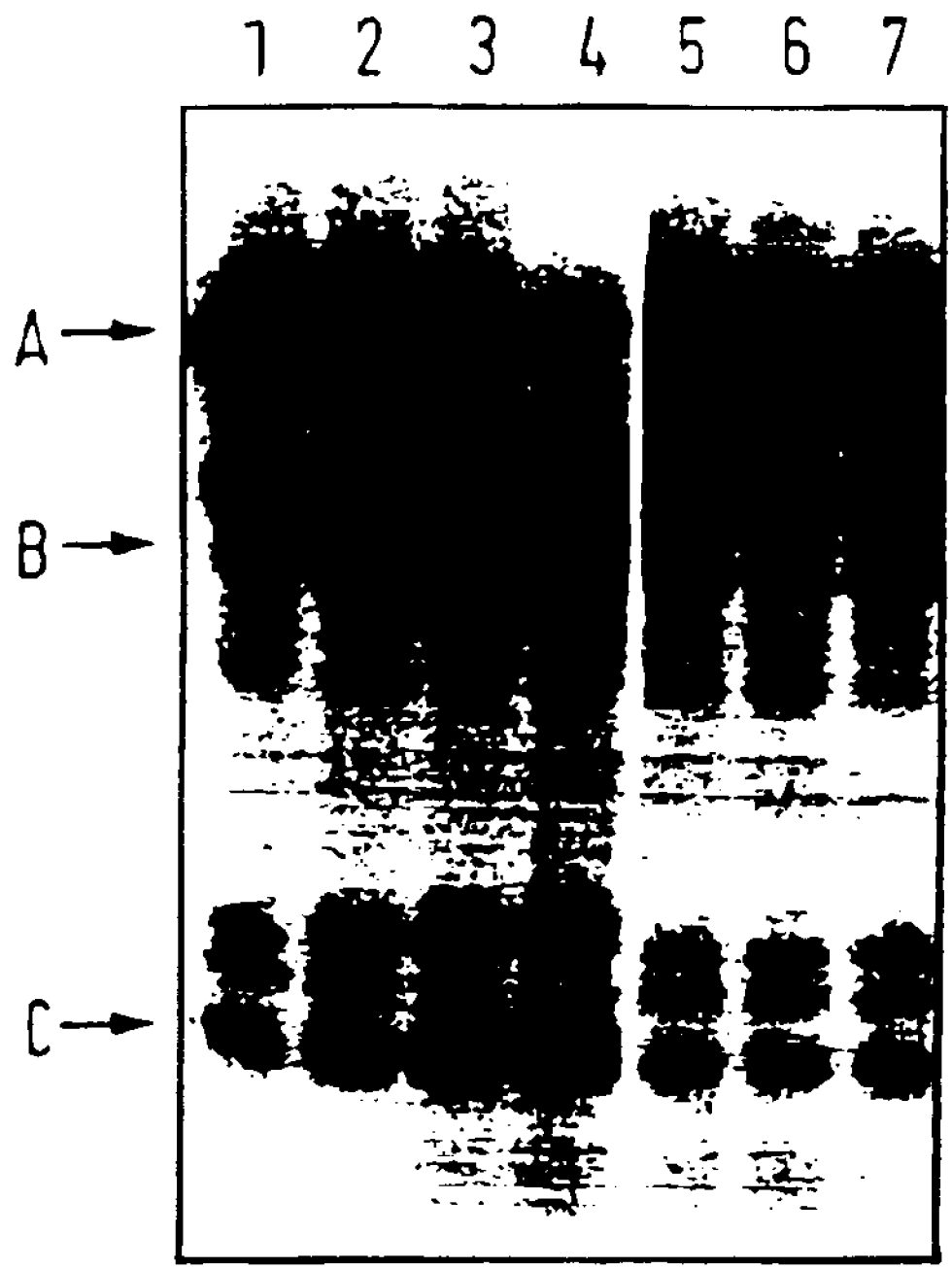

FIG. 7: shows an analysis of the cleavage of radiolabelled factor B by factor D, in the presence of wild-type and mutant C3's (C3i's).

A photograph of the autoradiograph of the SDS-PAGE gel is shown. All samples contained factor D and $^{125}$I-labelled factor B, and were incubated for 3 hours at 37° C.

The samples in the numbered tracks also included:

1. Buffer alone
2. 1/125 wild-type C3
3. 1/25 wild-type C3
4. 1/5 wild-type C3
5. 1/25 mutant C3 (residues 1427 Gln, 1431 Asp and 1433 Gln)
6. 1/5 mutant C3
7. undiluted mutant C3

The bands indicated by arrows are:

A. Uncleaved $^{125}$I-labelled factor B (93 kDa)

B. 60 kDa cleavage product ("Bb")

C. 33 kDa cleavage product ("Ba")

Figure 8:
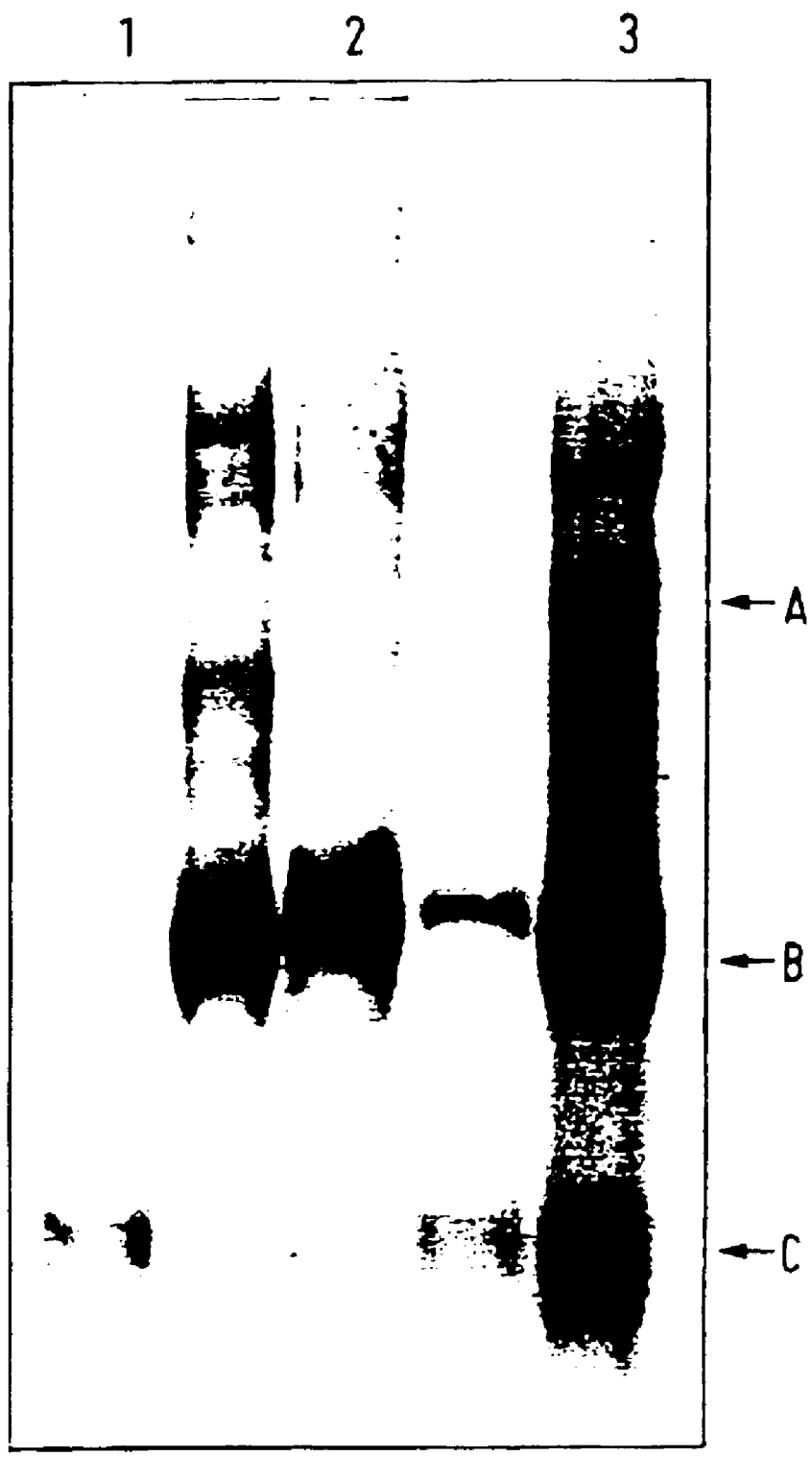

FIG. 8: shows an SDS-PAGE study illustrating the formation of a conjugate between C3i and IgG.

This is a Coomassie stain of a 4% acrylamide SDS-PAGE gel run under non-reducing conditions. The numbered tracks contain samples of:

1. PDP-IgG
2. C3i
3. PDP-IgG+C3i reaction mixture

Indicated by arrows are:

A. Probably C3i-IgG conjugate (350 kDa)

B. C3i (200 kDa)

C. IgG (150 kDa).

Figure 9:
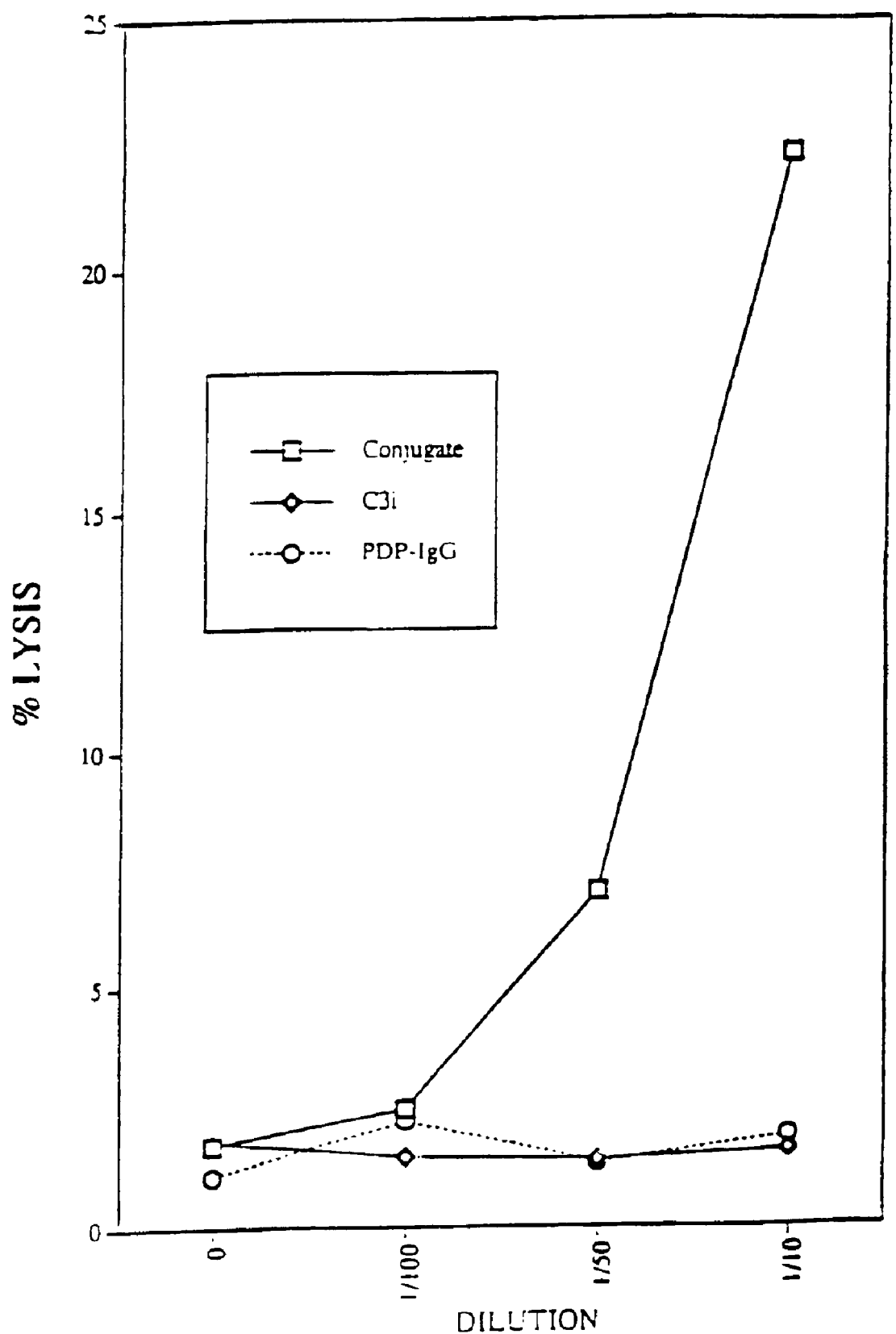

FIG. 9: demonstrates that conjugate targets C3 convertase activity against sheep erythrocytes.

(This graph shows the % lysed sheep erythrocytes after coating with dilutions of either the C3i-IgG conjugate, PDP-IgG or C3i followed by washing, generation of C3 convertases with properdin and factors B and D, and finally development of lysis by NGPS in CFD/EDTA, as described in the methods. Only the conjugate produces lysis, and this lysis is dose dependent.)

Figure 10:
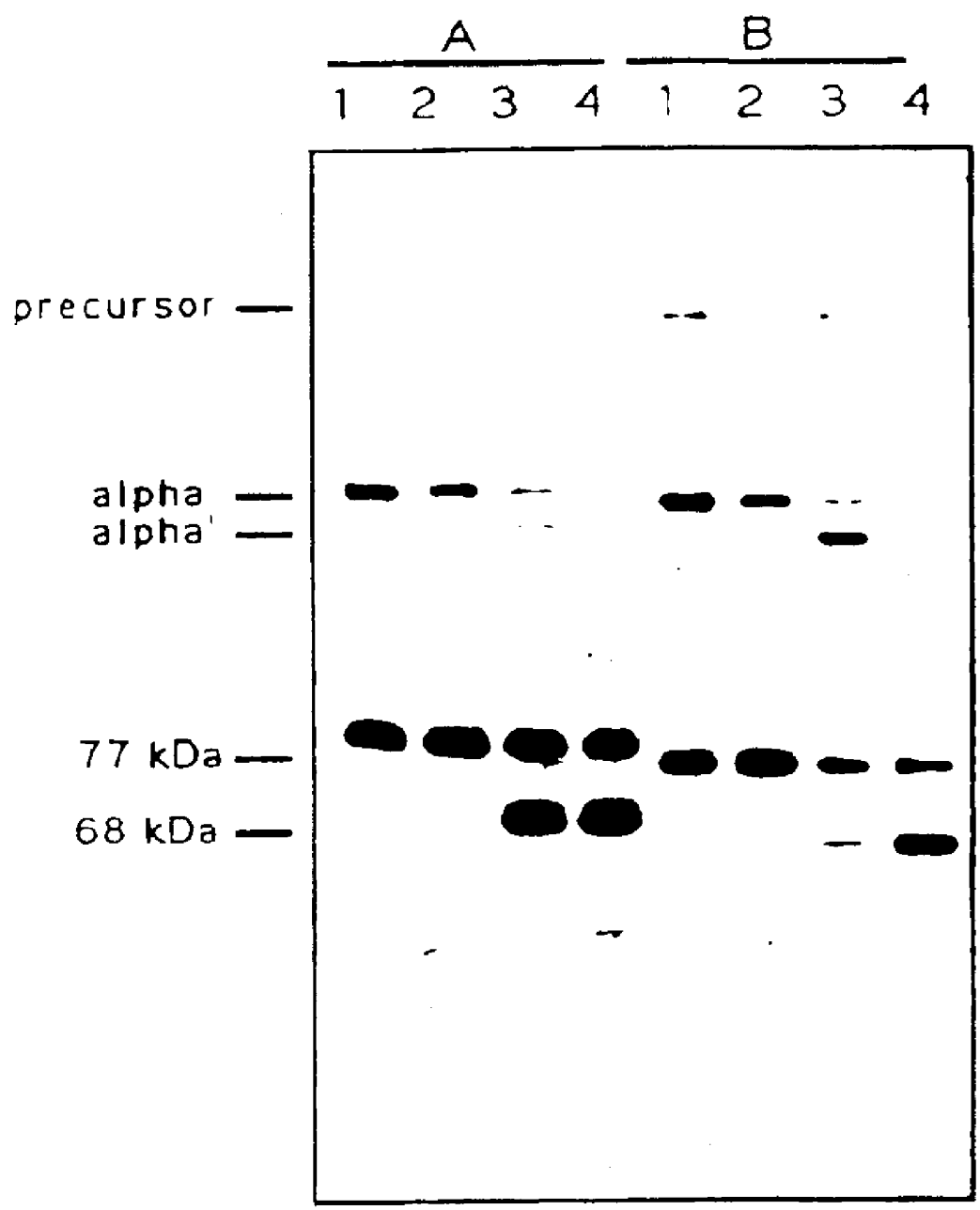
Figure 11:
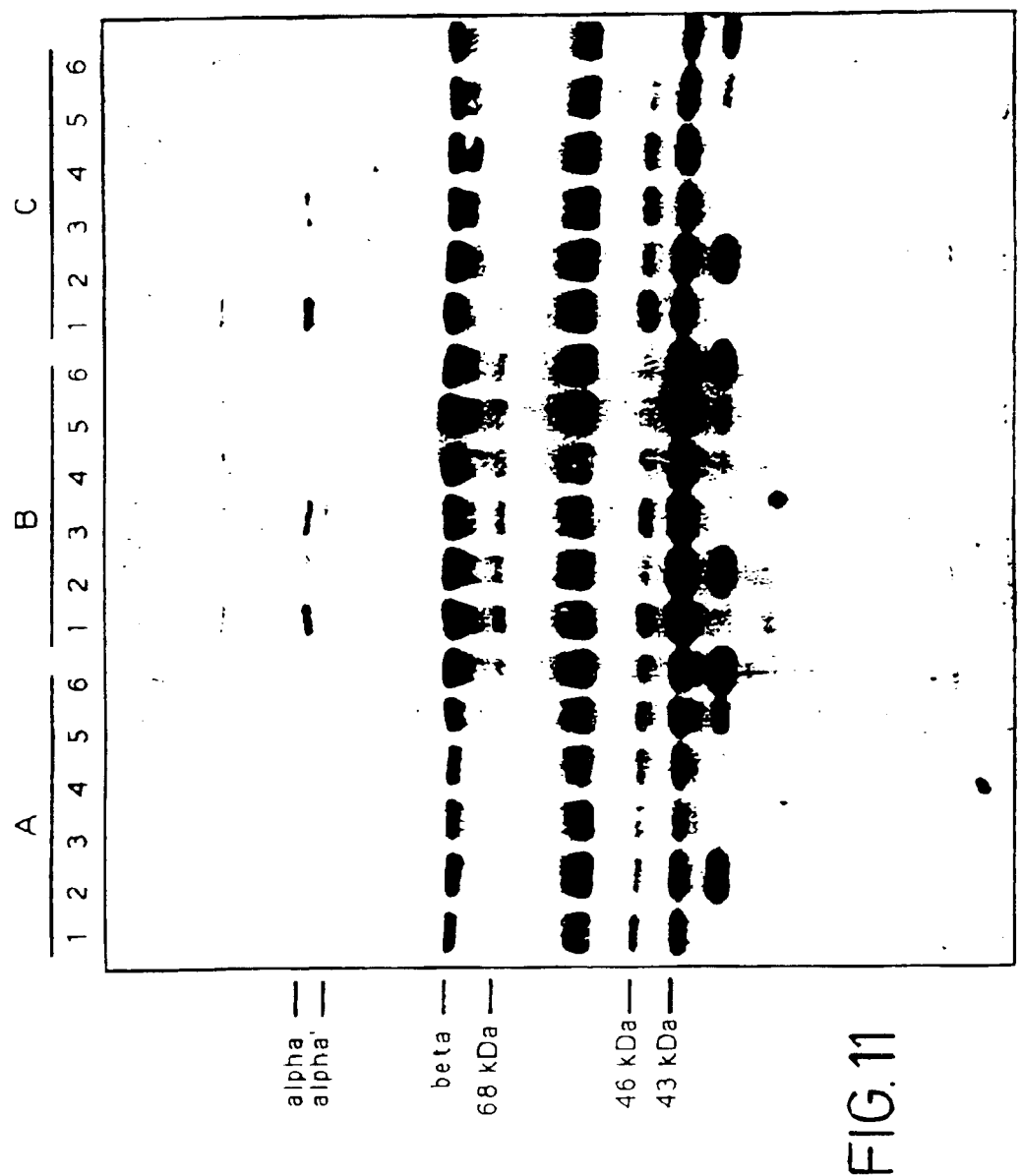

FIGS. 10 and 11: show the cleavage properties of the DV-1AM mutant C3 (see Examples 12–14).

In respect of FIG. 10, COS cell supernatants containing expressed wild-type (A) and DV-1AM mutant (B) C3 were treated with 1)-; 2) CVFBb; 3) 10 µg/ml factor I and 50 µg/ml factor H; or 4) CVFBb plus 10 µg/ml factor I and 50 µg/ml factor H, immunoprecipitated, analysed by SDS-PAGE (in the lanes indicated) and electroblotted onto nitrocellulose as described in example 4. In this case the blot was developed using a combination of rat monoclonal antibodies, Clone-3 and Clone-9, that react with the C3dg region of C3 and its fragmentation products (Lachmann, P. J. et al, *J Immunol*, 41:503 (1980)), followed by a horse radish peroxidase-coupled anti rat immunoglobulin (from Sigma) and detection using the ECL reagents and procedure supplied by Amersham.

In respect of FIG. 11, COS cell supernatants containing expressed DV-1B mutant (A), wild-type (B) and DV-6 mutant (C) C3 were treated with 1)-; 2) 10 µg/ml factor I and 50 µg/ml factor H; 3) CVFBb; 4) CVFBb plus 10 µg/ml factor I and 2 µg/ml factor H; 5) CVFBb plus 10 µg/ml factor I and 10 µg/ml factor H; or 6) CVFBb plus 10 µg/ml factor I and 50 µg/ml factor H; immunoprecipitated, analysed by SDS-PAGE (in the lanes indicated), electroblotted onto nitrocellulose and detected using a polyclonal sheep anti-C3 antibody as described in example 4.

Figure 12:

FIG. 12 shows an analysis of a C3 related product resulting from a frame shift mutation. This product is referred to as HDV-3X. Results for HDV-3X are compared with results for DV-3, which like HDV-3X includes the mutations T1031G, E1032N, Q1033H, E1035N and K1036I, but unlike HDV-3X is not modified at the C-terminus.

COS cell supernatants containing expressed DV-3 (A) and HDV-3X mutant (B) C3 were treated with 1)-; 2) CVFBb+10 µg/ml Factor I; 3) CVFb+10 µg/ml Factor I+1 µg/ml Factor H;, 4) CVFBb+10 µg/ml Factor I+5 µg/ml Factor H; 5) CVFBb+10 µg/ml Factor I+25 µg/ml Factor H; immunoprecipitated, analysed by SDS-PAGE (in the lanes indicated) and electroblotted onto nitrocellulose as described in example 4. In this case the blot was developed using a combination of rat monoclonal antibodies, Clone-3 and Clone-9, that react with the C3dg region of C3 and its fragmentation products (Lachmann, P. J. et al, 1980, J. Immunol. 41:503), followed by a horse radish peroxidase-coupled anti rat immunoglobulin (from Sigma) and detection using the ECL reagents and procedure supplied by Amersham.

Figure 13:
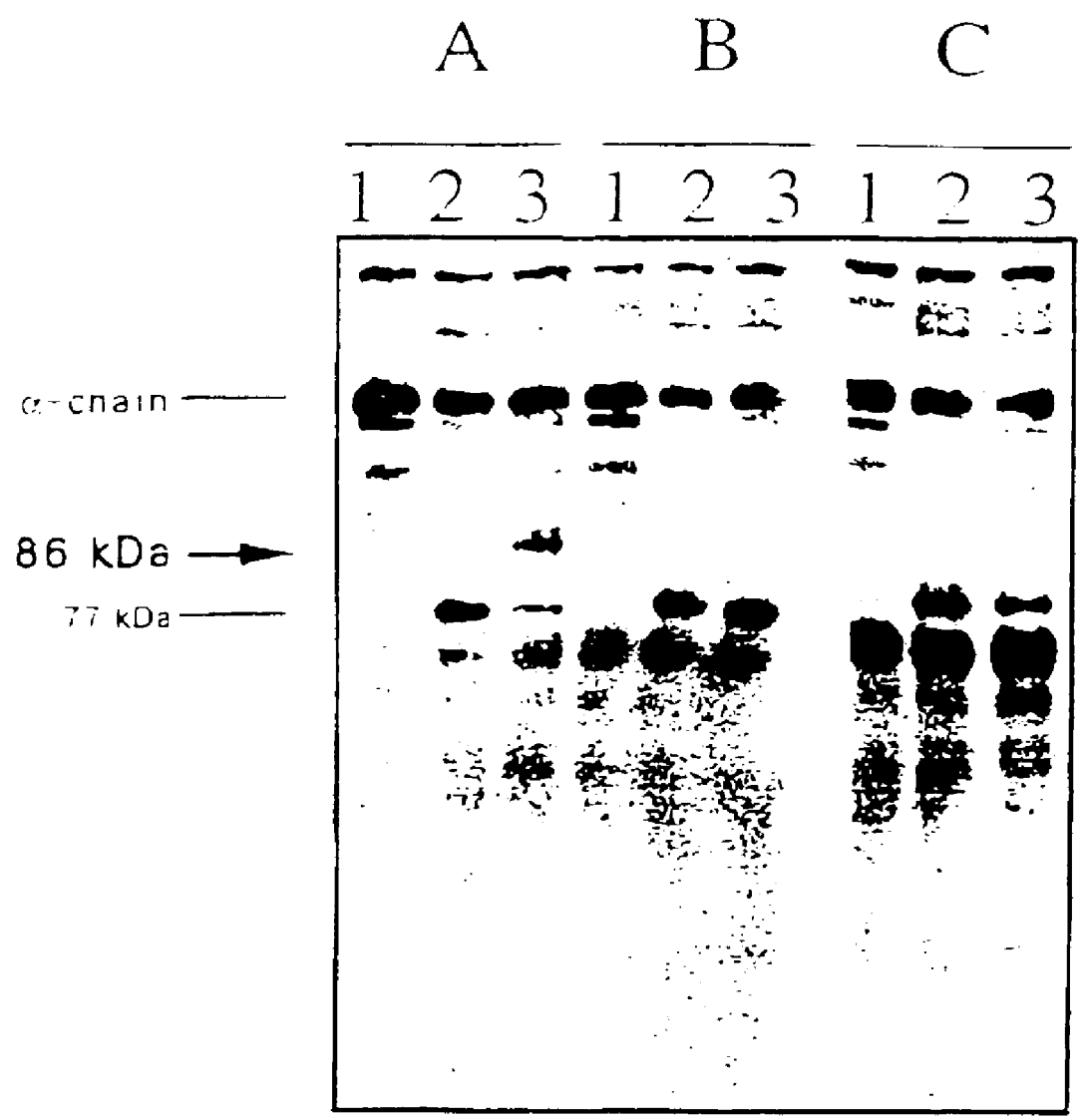

FIG. 13 is in respect of an experiment where COS cell supernatants containing expressed E1Q2(A), E1Q2QG3 (B) and E1Q2E3 (C) mutant C3 which were treated (37° C., 2.5 hr) with 1) CVFBb+10 µg/ml Factor I; 2) CVFBb+10 µg/ml Factor I+50 µg/ml Factor H; 3) CVFBb+10 µg/ml Factor I+25 µg/ml sCR1; immunoprecipitated, analysed by SDS-PAGE (in the lanes indicated) and electroblotted onto nitrocellulose as described in example 4. In this case the blot was developed using a combination of rat monoclonal antibodies, Clone-3 and Clone-9, as described in example 12, followed by a horse radish peroxidase-coupled anti rat immunoglobulin (from Sigma) and detection using the ECL reagents and procedure supplied by Amersham.

The 86 kDa band (arrowed) is the product of Factor I mediated cleavage at the third site when there has been no prior cleavage at sites 1 or 2.

Figure 14:
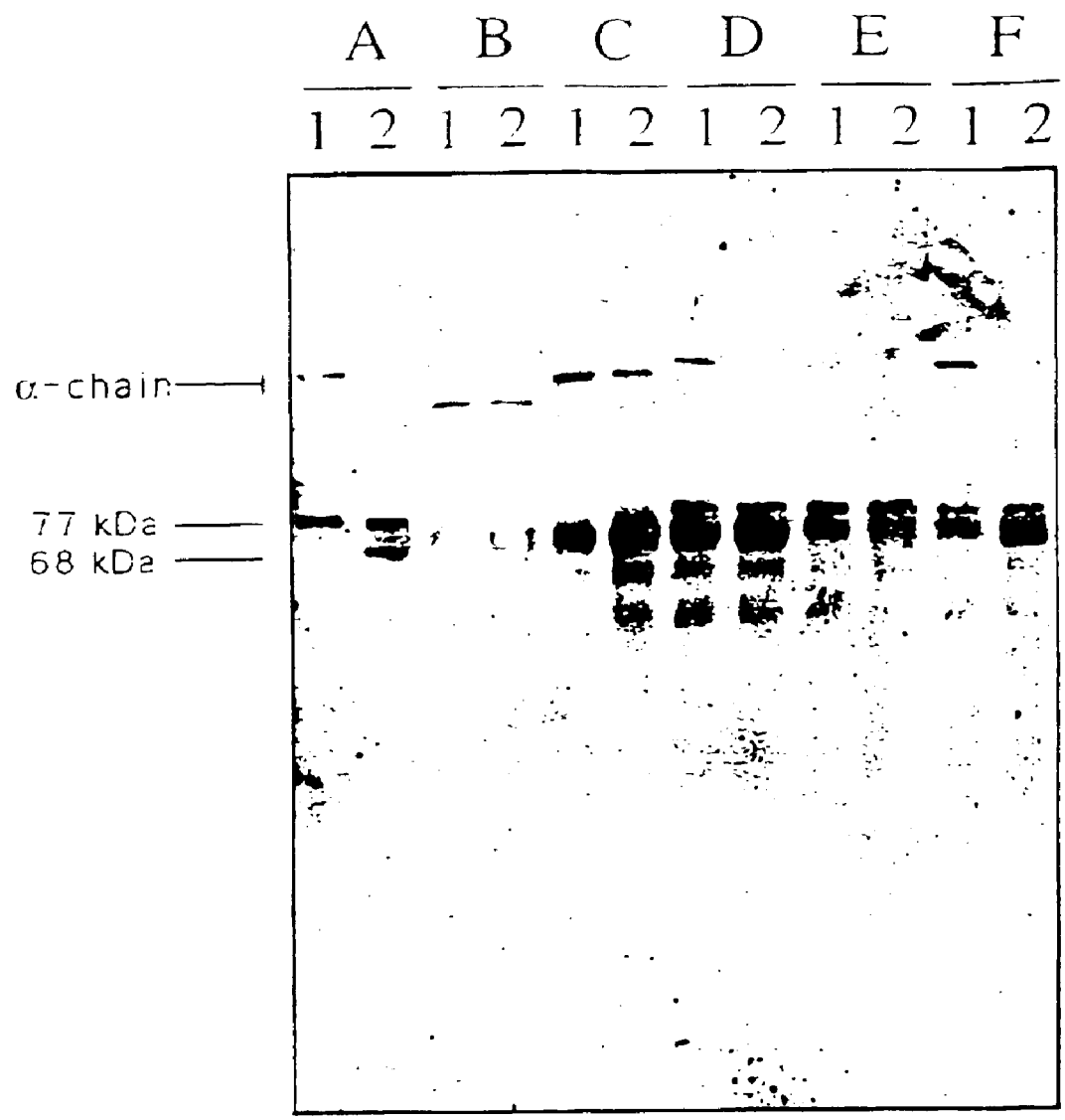

FIG. 14 is in respect of an experiment where COS cell supernatants containing expressed NC3 (A), FT-1 (B), FT-2 (C), FT-3 (D), FT-4 (E) and FT-5 (F) mutant C3 were treated (37° C., 2.75 hr) with 1)-; 2) CVFBb+10 µg/ml Factor I+50 µg/ml Factor H; immunoprecipitated, analysed by SDS-PAGE (in the lanes indicated) and electroblotted onto nitrocellulose as described in example 4. The blot was developed using a combination of rat monoclonal antibodies, Clone-3 and Clone-9, as described in example 12, followed by a horse radish peroxidase-coupled anti rat immunoglobulin (from Sigma) and detection using the ECL reagents and procedure supplied by Amersham.

Figure 15:
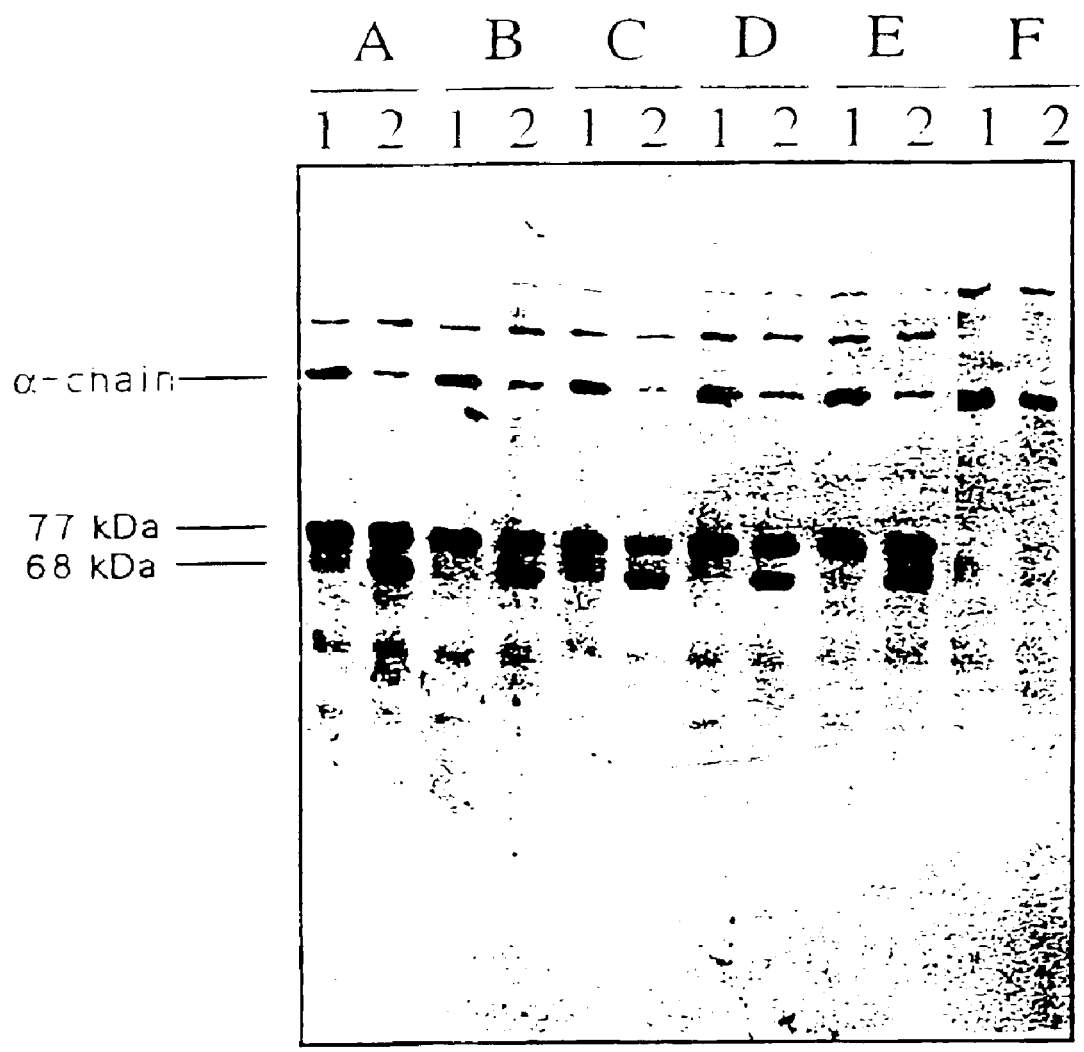

FIG. 15 is in respect of an experiment where COS cell supernatants containing expressed NC3 (A), FR-1 (B), FR-2 (C), FR-3 (D), FR-4 (E) and FT-2 (F) mutant C3 were treated (37° C., 2.5 hr) with 1)-; 2) CVFBb+10 µg/ml Factor I+50 µg/ml Factor H; immunoprecipitated, analysed by SDS-PAGE (in the lanes indicated) and electroblotted onto nitrocellulose as described in example 4. The blot was developed using a combination of rat monoclonal antibodies, Clone-3 and Clone-9, as described in example 12, followed by a horse radish peroxidase-coupled anti rat immunoglobulin (from Sigma) and detection using the ECL reagents and procedure supplied by Amersham.

For ease of reference, the relationship between the claims on file which relate to particular proteins capable of acting as down-regulation resistant C3 convertases and the examples and tables provided hereafter is set out below:

TABLE A

| Claims | Region of amino acid sequence (relative to human C3 convertase) believed to be important for down-regulation resistance | Example | Table |
|---|---|---|---|
| 5–8 | 1303/1320 | 1–6, 11 | |
| 9–11 | 758–780/752–754 | 7 | |
| 12 | 1427, 1431, 1433 | 8 | I |
| 13–15 | 992–1005 | 12, 13 | II |
| 16–19 | 1152–1155 | 14 | II |
| 20–29 | 1546–1663 | 15, 17 | III |
| 30–34 | 954–955 | 16 | |

The following standard methods and definitions are applicable to all the examples:

All complement components referred to are of human origin, unless otherwise specified, using standard terminology for all proteins and their derived fragments (e.g. as contained in reference [15]). In addition the term "C3i" refers to any molecular form of C3 without an intact thiolester bond, but retaining the C3a polypeptide on the alpha chain.

The human C3 cDNA and coding sequence are numbered as shown in FIG. 2, using the numbering used in the EMBL nucleotide data base (derived from reference [2]). The sequence shown is that of our construct ('PC3'), which lacks the first 11 nucleotides of the 5' untranslated region reported in reference [2], and hence the first base is numbered 12. The putative initiation codon is nucleotides number 61–63, the codon for the amino-terminal serine residue of the beta-chain is nucleotides 127–129, and the codon for the amino-terminal serine residue of the alpha-chain is nucleotides 2074–2076.

The protein sequence is numbered according to the precursor sequence as shown in FIG. 1 SEQ ID NO:22, which is a predicted translation of the DNA sequence in FIG. 2 (SEQ ID NO: 23) (amino acids 1–22 are expected to comprise a signal sequence that is removed during biosynthesis, and amino acids 668–671 are expected to be removed when the precursor is cleaved into the alpha and beta chains).

The following abbreviations have the following meanings; CVF cobra venom factor; ELISA, Enzyme-linked immunoadsorbant assay; E. coli, Escherichia coli; kb, kilobase; HSV-1, herpes simplex virus type 1; PBS, phosphate-buffered saline. COS-1 is a cell line derived from monkey kidney cells. The following are restriction endonucleases:—AflII, DraI, DraIII, EcoRI, EcoRV, HindIII, NaeI, NheI, XbaI.

STANDARD METHODS

Methods for standard molecular biological procedures such as plasmid isolations, agarose gel electrophoresis, and DNA ligations can be found in reference [21]. Double stranded DNA was sequenced using the 'Sequenase version 2.0' kit supplied by 'United States Biochemicals'. C3 expression was measured by an ELISA assay using plastic plates pre-coated with affinity-purified polyclonal sheep anti-human C3 to which samples of culture supernatant were added. Bound C3 was detected with a monoclonal rat antibody to C3 conjugated to alkaline phosphatase, and the chromogenic substrate, p-nitrophenol phosphate. Assays were calibrated with purified human plasma C3.

Methods for purification of complement proteins and CVF, and for the preparation of affinity purified anti-C3 antibodies used in the analysis can be found in reference [28]. Equivalent reagents can also be purchased from Sigma chemical company LTD.

C3 cDNA Coding Sequence

Our C3 cDNA coding sequence was constructed from two segments isolated from a random-primed human liver cDNA library carried in the vector pGEM4 (Promega). Five oligodeoxynucleotides, corresponding to known segments in the human C3 coding sequence, were radiolabeled with T4 polynucleotide kinase and [γ-32P]ATP and used to probe filter transfers of the library from agarose plates. Two clones containing inserts of approximately 4 kb were isolated. Restriction endonuclease digestion, hybridisation to specific oligodeoxynucleotide probes and partial sequence analysis demonstrated that one of these ('A13') included the 5'-end of the 5.1 kb message, whereas the other ('B44') extended to the 3'-end.

These inserts therefore overlapped by approximately 3 kb, including a unique EcoRI restriction enzyme site. The incomplete 5' section of A13 was cut out with EcoRI and NheI, and replaced with the complete segment isolated from B44 by digestion with EcoRI and XbaI. Both pieces were purified by gel electrophoresis in low-melting point agarose before ligating together with T4 DNA ligase to produce a vector ('PGC3') containing 5.1 kb of DNA encoding the entire C3 precursor protein.

Linker sequences 5' to the C3 coding region contained two ATG's which are potential false translation start sites. These were therefore removed by gapped-plasmid mutagenesis, as described in the method of example 1, using an oligodeoxynucleotide PL-ATC-3 (tagggagacc ggaagcttgc cctctccctc tgtccctctg t) (SEQ ID NO: 1) that deleted approximately 50 base pairs of linker/adaptor DNA, without altering the C3 coding sequence. This mutated vector, 7.7 kb containing 5.1 kb of C3 cDNA sequence plus 2.6 kb of sequence from the PGEM4 vector (Promega) is referred to as PC3.

The C3 coding region of the PGC3 plasmid was completely sequenced and revealed only four differences from a previously published human C3 ("S" allele) cDNA sequence [2].

(i) the changes C2481->G, and C2805->T do not alter the coding;
(ii) T1001->C encodes the previously described HAV 4-1-(Leucine314->Proline) polymorphic form [20]; and
(iii) G2716->A encodes Valine886->Isoleucine, that has not been previously reported in human C3, although Ile is found in this position in mouse and rat C3.

Our sequence includes start and stop codons, with a complete signal sequence and should, therefore, encode functional C3.

Levels of up to 1.7 µg/ml expressed wild type C3 in culture supernatants of COS-1 cells (transfected using liofectamine and the pcDNA3 (Invitrogen) expression vector) have been detected by ELISA. No detectable C3 was produced by cells transfected with pcDNA3 vector alone. Furthermore, analysis of the expressed product by cleavage reactions followed by immunoprecipitation, SDS-PAGE and immunoblotting demonstrated that:

(i) the primary translation product had been correctly processed into the mature two-chain form;
(ii) this product was, like native C3, cleavable to C3b by C3 convertase (CVFBb); and
(iii) the expressed protein was, like native C3, not cleavable by factor H plus I, but became cleavable after conversion to C3b by C3 convertase enzyme. This confirms that our starting plasmid can be translated into functional C3.

For an alternative description of a construction and expression of a C3 coding sequence see reference [25]).

EXAMPLE 1

Production of C3 that has the Arginine Residues at Both Factor I Cleavage Sites (Amino Acid Positions 1303 and 1320) Converted to Glutamine Residues to Prevent Cleavage of the C3b Fragment by Factor I a) Mutagenesis Mutagenic oligodeoxynucleotides used were QRI1 (caactgcccagccaaagctccaagatcacc) (SEQ ID NO: 2), QRI12 (gccagcctcctgcaatcagaagagaccaag) (SEQ ID NO: 3), and AFL4149 (taataaattcgaccttaaggtcaccataaaac) (SEQ ID NO: 4), as well as the corresponding antisense oligodeoxynucleotides—QRI1n (ggtgatcttggagctttggctgggcagttg) (SEQ ID NO: 15), QRI2n (cttggtctcttctgattgcaggaggctggc) (SEQ ID NO: 6) and AFL4149n (gttttatggtgaccttaaggtcgaatttatta) (SEQ ID NO: 7).

QRI1 and QRI1n specify the replacement of arginine for glutamine at the factor I cleavage site at amino acid residue 1303 in the C3 precursor sequence (by changing G3968C3969 to AA in the cDNA sequence), and QRI2 and QRI2n effect the same substitution at the factor cleavage site at amino acid residue 1320 (by changing nucleotide G4019 to A).

AFL4149 and AFL4149n introduce a cleavage site for the restriction endonuclease AflII at position 4149 in the cDNA sequence (by changing C4149 to T) without altering the encoded amino acid sequence. These two primers were used as markers, allowing successful mutagenesis to be identified on the basis of cleavage of the DNA product by AflII.

Mutagenesis was effected using the 'gapped plasmid' method. A batch of PGC3 ('UPGC3'), enriched in uridine in place of thymidine, was prepared by growth in *E. Coli* strain CJ236 in the presence of 0.25 μg/ml uridine. This plasmid was digested with SmaI and the 7.2 kb product ('US1') agarose gel purified to remove a 0.5 kb fragment from the C3 sequence (residues 1463–1947). The other component of the gapped plasmid ('DN2') was prepared by digesting PGC3 with DraIII plus NaeI and purifying the 5.1 kb piece twice by agarose gel electrophoresis. 200 ng DN2 was mixed with approximately 500 ng US1 in 50 μl H2O, heated to 100° C. and cooled slowly to below 50° C., before adding 20 μl to 25 μl of 2×T7 buffer (100 mM Tris/HCl/pH 7.4/14 mM MgCl2, 100 mM NaCl, 2 mM dithiothreitol, and 1 mM each of ATP, dATP, dCTP, dTTP and dGTP) plus 10 nmol of each 5'-phosphorylated mutagenic primer (one reaction used QRI1, QRI2 plus AFL4149, another reaction used QRI1n, QRI2n plus AFL4149n). The mixtures were reheated to 70° C. for 5 min and cooled slowly (over 30–60 min) to 20° C. At 0° C., 10 units of T7 DNA polymerase plus 80 units T4 DNA ligase are added. The mixture (total volume 50 μl) was incubated first at 0° C., for 5 min, then at room temperature for 5 min, and finally at 37° C. for 3 hours. 1 μl of each mixture was used to transform 100 μl supercompetent XL1 *E. Coli* (Stratagene) according to the manufacturer's instructions.

Ampicillin resistant colonies were screened for AflII cleavage, and successful mutants were grown up in 100 ml cultures from which the plasmids were isolated and sequenced (using a sequencing primer C3pa-3876, cttcatggtgttccaagcct (SEQ ID NO: 24), matching nucleotides 3876–3895 of C3 cDNA) to characterise mutations at the factor I cleavage sites.

For an alternative protocol for "gapped plasmid" mutagenesis see references [26, 27].

b) Transfer of Mutant DNA to Eukaryotic Expression Vector

The C3 coding fragments from mutant plasmids were excised by double digestion with HindIII and NaeI. DraI was also included to incapacitate the residual plasmid. The C3 coding sequence was agarose gel purified and ligated into pcDNA3 vector (Invitrogen) that had been linearised with HindIII and EcoRV enzymes and dephosphorylated with calf intestinal phosphorylase. Ligation mixtures were used to transform supercompetent XL1 *E. coli,* which were then plated onto culture plates containing ampicillin.

A random selection (three or four) of ampicillin resistant colonies were grown up in 2–3 ml cultures and small scale isolation of the plasmid DNA. The plasmids containing the correct insert were identified by digestion of the plasmid DNA with restriction endonucleases EcoRI, HindIII and AflII. The corresponding colonies grown up in 100 ml cultures and the plasmids purified by the standard procedure. These mutants were originally constructed from PGC3 and so retained the two ATG's 5' to the coding region. This region (plus the 5' 3 kb of the C3 coding sequence) was therefore excised with HindIII plus EcoRI and replaced by ligation of the same segment cut out of PC3. These reconstructed vectors were prepared by the standard procedure and used for transfection of COS cells.

c) Expression of Wild-type and Mutant C3's

Mutants and wild-type C3 were transiently expressed from plasmids transfected into COS-1 cells using lipofectamine® (GIBCO) according to the manufacturer's instructions. Typically, 1–1.5×$10^5$ cells per well of a standard 6 well culture plate were transfected with 2–4 μg of plasmid using 9 μl of lipofectamine reagent. Supernatants were assayed for C3 secretion, and typical yields of 0.3–1.7 μg per ml supernatant were obtained 3–6 days after transfection.

Results a) Generation of Mutants

The following mutants, named according to the mutagenic oligodeoxynucleotide sequences that have been incorporated, have so far been isolated:

(i) 3 mutants with both QRI1 and QRI2 mutations plus AFL4149: C3M-26, C3M-58 and C3M-61;

(ii) 1 mutant with QRI1 and QRI2 but without AFL4149: C3M-8; and (iii) 1 mutant with QRI2 and AFL4149, but without QRI1: C3M-51 (used in example 3).

b) Validation that Functional Effects were Due to the Mutations Specifically Introduced at the Factor I Cleavage Sites Sequencing has confirmed the absence of other alterations in 178–350 bases around the mutated region of each mutant. The sequence of one mutant produced by this procedure, C3M-51 (see example 3), has been analysed throughout the entire 'gap' (bases 2463–5067) used in mutagenesis, and no other deviations from the wild-type sequence were found.

Furthermore, representative sequencing of a total of 2922 bases from all mutants have not revealed any single point mutations that could have been caused by polymerase-mediated errors. The expressed mutants all displayed the two-chain structure and cleavage by C3 convertases characteristic of native C3. In summary, the mutants used are unlikely to contain any unwanted changes although they have not been completely re-sequenced.

EXAMPLE 2

Production of C3 that has the Arginine Residue at One Factor I Cleavage Site (Amino Acid Position 1303) Converted to a Glutamine Residue The procedure of Example 1 was followed except that only mutagenic oligodeoxynucleotides AFL4149 plus QRI1 or AFL4149n plus QRI1n (i.e. no QRI2 or QRI2n), were used in mutagenesis.
Results
a) Mutants Obtained
2 mutants with QRI1 and AFL4149 but without QRI2 were isolated:—C3M-I23,27. The mutant C3M-I23 was expressed, as described in Example 1.

This protein was cleavable by CVFBb. The C3b-like product was relatively (compared to the wild-type) resistant to cleavage at position 1303 by factors I and H, but could still be cleaved at position 1320. This C3b derivative is therefore partially resistant to factor I.

EXAMPLE 3

Production of C3 that has the Arginine Residue at One Factor I Cleavage Site (Amino Acid Position 1320) Converted to a Glutamine Residue The procedure of Example 1 was followed except that only mutagenic oligodeoxynucleotides AFL4149 plus QRI2 or AFL4149n plus QRI2n (i.e. no QRI1 or QRI1n), were used in mutagenesis. In addition, the method used in example 1 also yielded one mutant with QRI2 and AFL4149, but without QRI1.

Results a) Mutants Obtained 3 mutants with QRI2 and AFL4149 but without QRI1 were isolated:—C3M-51, C3M-Q2, C3M-Q13. The mutant C3M-51 was expressed, as described in Example 1. This protein was cleavable by CVFBb. The C3b-like product was not readily cleaved at position 1320 by factors I and H, but it could still be cleaved at position 1303. This C3b derivative is therefore partially resistant to factor I.

EXAMPLE 4

Analysis of the Functional Effects of Mutations

Supernatants (100–400 μl) from transfected COS cells were incubated at 37° C. for 2 h with:

COS cells were transfected with pcDNA3 carrying inserts of:

1) the unmutated C3 sequence;

2) mutant C3M-I23 (encoding $Arg^{1303}$->Gln);

3) mutant C3M-26 (encoding $Arg^{1303}$->Gln, $Arg^{1320}$->Gln); and 4) mutant C3M-51 (encoding $Arg^{1320}$->Gln).

200 μl of the culture supernatants, taken 3 days after transfection, were pretreated with 2 mM phenylmethanesulphonyl fluoride (0° C., 15 min) and then incubated at 37° C. for 2 hours with the following:

A) no addition;

B) preformed C3 convertase, CVFBb (10 μl from 200 μl containing 6.6 μg CVF, 100 μg factor B and 1.4 μg Factor D in phosphate-buffered saline (PBS) containing 10 mM $MgCl_2$, preincubated at 37° C., 15 mins);

C) factors H (5 μg) and I (1 μg); and

D) CVFBb plus factors H and I.

These were then immunoprecipitated by adding 0.6 μg affinity-purified sheep anti-human C3 immunoglobulin at room temperature and after 1 hour adding 20 μl a 5% suspension of washed formalin-fixed Group C *Streptococcus* sp. cells (protein G) (Sigma). After 45 min at room temperature the particles were washed once in PBS, 5 mM $NaN_3$, and once in 20 mM Tris/HCl, 137 mM NaCl, 0.1% (v/v) Tween 20, pH 7.6 before eluting in 1% SDS/2% 2-mercaptoethanol (90–100° C., 5 min). These eluates were separated by SDS-PAGE, electroblotted onto nitrocellulose and the C3 bands detected by probing with affinity-purified sheep anti-human C3 immunoglobulin followed by horse radish peroxidase-coupled donkey anti-sheep immunoglobulin (Sigma) and detection using the "Enhanced Chemiluminescence" substrates supplied by Amersham. A photograph of a 2 minute exposure to X-ray film is shown. The visible C3-derived bands are indicated by labelled arrows, and the individual samples (1–4, A–D) are those just described. (The prominent band of about 50 kDa (between the 46 and 68 kDa bands) present in all samples is the heavy chain of the IgG used in the immunoprecipitation and detected by the horse radish peroxidase-coupled donkey anti-sheep immunoglobulin.).

Results (see FIG. 3)

1. All the untreated samples (1-A, 2-A, 3-A, 4-A) contain bands of the correct migration for alpha and beta chains of C3, indicating that all the mutants are expressed, and post-translationally processed correctly. The presence of 43 or 46 kDa bands in these samples indicates the presence of some factor H+factor I-like activity in the culture medium. Spontaneous hydrolysis of C3 during the 3 day biosynthetic period produces C3i which is cleaved by this activity. In the unmutated C3 this generates bands of 43 kDa and 75 kDa (the 75 kDa band is invisible because (i) it is hidden by the 75 kDa beta chain, and (ii) the antibody used to develop the western blot has very little activity towards this portion of the C3 alpha chain:-its presence was subsequently confirmed by reprobing with a rat monoclonal antibody, "Clone-3", that is specific for this region). The addition of factors H and I without CVFBb (1-C, 2-C, 3-C, 4-C), did not cleave the remaining C3 indicating that this represented active C3 (thiolester intact).

2. The unmutated C3 (1) is cleaved by CVFBb and the C3b product is further cleaved by endogenous enzymes in 1-B or added factors H and I in 1-D. The 43 kDa band indicates cleavage at $Arg^{1320}$, and the 68 kDa band (visible in longer exposures) indicates cleavage at $Arg^{1303}$.

3. The mutant C3M-I23 ($Arg^{1303}$->Gln) was cleavable by CVFBb and the product was relatively resistant to endogenous factor H and I-like activity (2-B), with distinct amounts of alpha' chain (C3b) persisting, but was still cleavable when extra factor H and I were added (2-D). The 43 kDa product indicates cleavage at $Arg^{1320}$, (a faint band at 71 kDa representing the other fragment of the alpha' chain could be seen in longer exposures) but no 68 kDa band was present, showing that this mutant is resistant to cleavage at the mutated $Gln^{1303}$.

4. The mutant C3M-26 ($Arg^{1303}$->Gln,$Arg^{1320}$->Gln) was cleavable by CVFBb and the C3b-like product (alpha') was resistant to endogenous factor H and I-like activity (3-B). It was also very resistant to the additional factors H and I (3-D) in comparison with the unmutated C3 (1) and other mutants (2 and 4). There was a small amount of 46 kDa product indicating some cleavage at the mutated $Gln^{1303}$ (the accompanying 68 kDa fragment was also visible on longer exposures). There was little or no detectable 43 kDa that would correspond to any cleavage at $Gln^{1320}$.

Therefore the Arg->Gln mutation at position 1303 is less effective than that at position 1320 at preventing cleavage by factor I. (This slow residual cleavage might also be occurring in the mutant C3M-I23 (Arg$^{1303}$->Gln), but the 46 kDa intermediate is probably being rapidly processed to 43 kDa by further cleavage at the unmutated Arg$^{1320}$.)

5. The mutant C3M-51 (Arg$^{1320}$->Gln) was cleavable by CVFBb and the product was cleaved by endogenous factor H and I-like activity (4-B), and by additional factor H and I (4-D). The 46 kDa product (and faint 68 kDa band) indicates cleavage at Arg$^{1303}$. However, the absence of a 43 kDa band indicates that it is not cleaved at the mutated Gln$^{1320}$.

EXAMPLE 5

Comparison of Various Amino Acid Substitutions at Position 1303

1. Introduction

The previous examples described mutations of arg 1303 and arg 1320 to glutamine residues. Both mutations imparted resistance to cleavage at those positions by factor I. However, there was a small but detectable degree of cleavage at gln 1303. Therefore a number of other amino acid substitutions at this position have been made and tested. Cleavage occurs, in decreasing order of efficacy when residue 1303 is: Arg>Tyr>[Cys or Trp]>Gln>[Glu or Gly]. These results are unexpected because (i) all known naturally occurring human factor I-mediated cleavages occur C-terminal to arginine residues, so it would have been deduced that the enzyme had a requirement for arginine; and (ii) if it did cleave at other residues one would predict that they would have to be electrostatically similar to arg, i.e. a basic residue (lys or his), (e.g. trypsin selectively cleaves C-terminal to arg, lys or his), so one could not have predicted cleavage of the tyrosine substitution.

Therefore substitution of arg 1303 with glycine or glutamic acid is preferred for the purpose of creating a derivative of C3 resistant to inactivation by factor I.

2. Methods 2.1 Mutagenesis: the degenerate mutagenic primer used was:

caactgcccagc (gt) (ag) (cg) agctccaagatcacc (SEQ ID NO: 8)(letters in brackets indicate mixture of bases at that position). Mutants were constructed either by the gapped-plasmid method (as described in the earlier examples), or by the "megaprimer method" (V. Picard et al, *Nuc Acid Res* 22:2587–91, (1994)), in which the upstream primer was caccaggaactgaatctagatgtgtccctc (SEQ ID NO: 9) and the downstream primer was gttttatggtgaccttaaggtcgaatttatta (SEQ ID NO: 10). All mutations were performed on templates in which the C3-encoding DNA had already been mutated such that amino acid residue 1320 was glutamine, and a restriction site for AflII had been introduced at position 4149 (as described in the earlier examples) and were confirmed by DNA sequencing.

2.2 Expression: mutants were expressed in COS cells using the pcDNA3 vector as described in the earlier examples, biosynthetically labelled with [$^{35}$S] methionine in serum-free medium.

2.3 Assay: the supernatants were treated wish CVFBb (formed by reaction of CVF with factors B and D in magnesium-containing buffer) and factors H and I followed by immunoprecipitation with anti-C3 and separation by SDS-polyacrylamide gel electrophoresis performed under reducing conditions (as described in the earlier examples). The gel was fixed, treated with Amersham "Amplify" reagent, dried and exposed to autoradiography film to yield the result shown in the figure.

3. Results

Factor I-mediated cleavage at position 1303 (site 1), without cleavage at 1320 (site 2) (where this has been mutated to glutamine) produces bands of 46 and 68 kDa. It can be seen that cleavage occurs in the order: arg(R)>tyr (Y)>cys(C) and trp(W)>gln(Q)>gly(G) and glu(E). The wild-type (arginine at both positions) is cleaved at both positions to produce fragments of 43 (too small to be visible on this gel) and 68 kDa.

4. Figure

The results are shown in FIG. 4. The residues at site 1 (position 1303) and site 2 (1320) are indicated above the respective tracks.

EXAMPLE 6

Demonstration of Enhanced Resistance to Inactivation by Factors I and H After Mutation of Arg 1303 to Gln 1. Introduction The earlier examples demonstrated that conversion of either arg 1303 or arg 1320 to glutamine made that site resistant to cleavage by factor I. Mutation of both sites makes a molecule that is resistant to cleavage at either site. Here, we further demonstrate that mutation of arg 1303 to gln alone (without alteration to arg 1320) results in a considerable resistance, compared to the wild-type, to functional inactivation by factors I and H.

2. Method 2.1 Expression: The preparation of the arg 1303->gln mutation was described in an earlier example. This was transfected into CHO (a common laboratory cell line derived from chinese hamster ovary cells) by the calcium phosphate method, and stable transfectants selected on the basis of resistance to G418 ("Geneticin" available from Sigma). Cell culture supernatants were collected, and the expressed C3 was partially purified by sodium sulphate precipitation (10–20% (w/v) fraction), and ion-exchange chromatography on Q-sepharose and mono-Q sepharose (A W Dodds *Methods Enzymnol* 223: 46 (1993)).

2.2 Assay: Sheep erythrocytes were coated with SO16 monoclonal antibody (R A Harrison and P J Lachmann *Handbook of Experimental Immunology* 4th Edition chpt. 39 (1986)) and 4.4 ml of a 5% (v/v) suspension was then incubated with approximately 10 µg C2, 24 µg C4 and 1 µg C1 (purified human components) for 10 min at 37° C. in CFD (R A Harrison and P J Lachman supra). 0.8 ml of this mixture was then incubated for 105 min with 0.25 ml containing the semi-purified mutant or wild-type C3 and EDTA to a final concentration of 12.5 mM. The cells were then washed in CFD and used in CFD containing 0.1% (w/v) gelatin (CFD-gel). Radioligand binding with [$^{125}$I]-labelled clone 4 monoclonal anti-C3 antibody was used to confirm that similar amounts of wild-type or mutant C3b were deposited.

For the assay, 40 µl of a 5% suspension of cells was diluted in 250 µl CFD-gel and 50 µl aliquots were incubated with 50 µl CFD-gel containing dilutions of factors I and H to final concentrations of 100, 10, 1 and 0 µg/ml each, at 37° C. for 30 min. 0.9 ml of CFD was then added, the cells pelleted by centrifugation and washed twice more with 1 ml of CFD each time. The cells were then resuspended in 100 µl CFD-gel containing 100 µg/ml factor B, 100 µg/ml properdin, 1 µg/ml factor D and 0.3 mM NiCl$_2$. After 10 minutes at 37° C., 0.9 ml of CFD containing 10 mM EDTA and 2% (v/v) normal guinea-pig serum. After a further 30 min at 37° C., unlysed cells were pelletted by centrifugation, and the degree of lysis determined by measuring the absorbance of the supernatant at 412 nm. The absorbance equivalent to 100% lysis was determined from an aliquot of cells lysed in water, and hence the percentage lysis was calculated.

This assay measures the ability of deposited C3b to form a functional C3bBbP convertase. Conversion to iC3b prevents convertase formation and subsequent lysis in serum/EDTA.

3. Results

The result shown in the figure indicates that more than ten times as much factor I and factor H are required to abrogate the hemolytic activity of the arg 1303->gln mutant, when compared to the wild-type. This mutation is therefore advantageous for the creation of a derivative of C3 whose C3b product is resistant to inactivation by factors H and I. The effect could either be due to the greater resistance to cleavage at position 1303 (when arg is mutated to gln), or to greater resistance to cleavage at position 1320 when cleavage can first take place at position 1303.

4. Figure

The results are shown in FIG. 5. The x-axis indicates the concentration of factors H and I. Q1 represents the arg 1303->gln mutation. % lysis is measured as described in the methods.

Discussion

The essential features of Human C3, with respect to modified variants described herein are as follows:

(i) The molecule has a functionally C3b-like derivative in that it can combine with functionally active human factor B, which can then be cleaved by human factor D to form an enzyme capable of cleaving human C3.

(ii) the amino acid sequences of derivatives are more homologous to C3 from humans than to C3 from any other species for which a sequence is presently known, or to any other presently known protein sequence. Structural features of C3 present in wild-type protein, but not necessarily in modified derivatives, include the following:

(a) The DNA coding sequence and translated protein sequence for the variant of human C3 used in the examples of the invention described herein are given in FIGS. 2 and 1 respectively. This protein sequence differs from the published sequence [2] at just two amino acids (details are given in the examples). It is assumed that many more variations are compatible with C3 function, even though most will not be present in the population.

(b) The primary translation product is proteolytically processed into two disulphide-linked chains, alpha (residues 672–1663) and beta (residues 23–667), with removal of the signal sequence (residues 1–22).

(c) The mature protein contains a thiolester bond between residues Cys1010 and Gln1013.

(d) C3 convertases cleave C3 to remove C3a (residues 672–748). This reaction is followed by breakage of the thiolester bond.

(e) In the presence of factor H, factor I cleaves C3b between residues Arg1303 and Ser1304, and between Arg1320 and Ser1321.

Modifications Made to the Native C3 Molecule

Replacement of Arg1303 by Gln

This modification is at one site of cleavage of C3b by factor I. The effect is to reduce the rate of cleavage by factor I at this position. The change to glutamine was selected to take away the positive charge of the arginine, which is likely to be important for the serine protease activity of factor I, while retaining a hydrophilic character and a similar side-chain size that should minimise any disruptions to the tertiary protein structure. Evidence supporting this presumption is that the mutation did not prevent processing into a two-chain structure, formation of a thiolester or cleavage of C3 by C3 convertase. Mutation of Arg1303 to another amino acid can achieve a similar or even a superior effect, as demonstrated in Example 5.

It may also be possible to reduce this cleavage by mutating Ser1304 (the other side of the cleavage site) or other residues involved in the enzyme-substrate interaction.

Replacement of Arg1320 by Gln

This modification is at the other site of cleavage of C3b by factor I. The effect is to drastically reduce (virtually abolish) the rate of cleavage by factor I at this position. The change to glutamine was made on the same criteria described above, and this mutation also did not prevent processing into a two-chain structure, formation of a thiolester or cleavage of C3 by C3 convertase. Again, mutation to another amino acid may achieve the same effect, as may mutation of Ser1321 or other residues involved in the enzyme-substrate interaction.

When in combination the two mutations, Arg1303-Gln and Arg1320-Gln, protect the C3b from inactivation and hence maintain its ability to form part of an active C3bBb convertase. Other mutations (including combinations of mutations) that abolish both cleavage reactions could also be used (for example Arg 1303 Glu or Arg 1303 Gly could be used in combination with Arg 1320 Gln).

EXAMPLE 7

Various Mutations that Reduce the Interaction of C3b/C3i with Factor H 7.1 Introduction Other laboratories have produced evidence based either on the effects of synthetic peptides (Ganu, V. S. and Muller-Eberhard, H. J., 1985, *Complement* 2:27; Becherer, J. D. et al., 1992, *Biochemistry* 31: 1787–1794), or limited mutagenesis (Taniguchi-Sidle, A. and Isenman, D. E., 1994 *J. Immunol.* 153: 5285–5302) to suggest that the residues 752–761 in the primary sequence of the C3 transcript (see FIG. 1) could be involved in the interaction with factor H. However, other published evidence suggests that only residues 767–776 are involved in the interaction with factor H, whereas residues 752–761 are important for the interaction with factor B (Fishelson, 1991, *Mol. Immunol.* 28:545–552). We surmised that more extensive mutagenesis of this region might reduce the affinity for factor H and therefore be desirable for the objective of creating a C3 derivative that is resistant to factor H. Furthermore, we guessed that the important residues to mutate could be the prominent acidic residues (aspartic and glutamic acids) and that it would be desirable to change them to neutral residues less likely to mediate strong interactions. In this example we changed residue 752–754 from Asp-Glu-Asp to Gly-Ser-Gly, in combination with changing residues 758–760 from Glu-Glu-Asn to Gly-Ser-Gly. The product displayed reduced cleavage characteristics consistent with a reduction in the susceptibility to factor H. This provides evidence that C3 can be modified to reduce the binding of factor H, and hence the susceptibility to factors H. and I. These modifications are desirable for the creation of a C3 convertase that is stable under physiological conditions.

7.2 Method

The methods of mutagenesis, expression and analysis have been described in the earlier examples. The mutagenic oligonucleotide that was synthesised had the sequence: agtaacctgggttcgggcatcattgcaggatcgggcatcgtttc (SEQ ID NO: 11).

7.3 Results

The results of cleavage reactions are shown in FIG. 6. These indicate that:
1. Addition of CVFBb to wild-type C3 results in elimination of the alpha chain (track 2) because the C3b that is formed is susceptible to the low concentrations of factor I and H in the culture supernatant. C3i that has been formed during expression or this subsequent incubation has been broken down to iC3i in the same way. Addition of exogenous factors I and H (tracks 3 and 4) are therefore no different from tracks 1 and 2 respectively, because the medium itself contains sufficient factor H and I activity to effect complete cleavage.
2. In contrast, treatment of the mutant C3 with CVFBb (track 6) does not result in disappearance of the alpha chain. There is some generation of alpha', corresponding to C3b, but some or all of this remains, indicating that the persistence of alpha chain is not merely the result of a failure of cleavage by CVFBb. The remaining uncleaved alpha chain in track 2 may therefore represent C3i that has not been cleaved by the endogenous activities of factors H and I, although it is also possible that some of this represents native C3 persisting if the mutant has acquired a partial resistance to CVFBb. Addition of high concentrations of exogenous factors H and I (track 7 and 8) does produce depletion of alpha and alpha' chains, indicating that (i) the mutant is not completely resistant to these factors, and (ii) the alpha chain uncleaved by CVFBb in track 2 is predominantly derived from C3i (which is cleavable by factors H and I but not by CVFBb) rather than from native C3 (which is cleavable by CVFBb but not by factors H and I). Still not all the alpha chain is cleaved, even in track 8, probably because of the resistance to factors H and I.

Therefore mutation of residues 752–754, and residues 758–760 can generate a C3 molecule that can still be cleaved by C3 convertases, but is partially resistant to the actions of factors H and I. In view of other published data, this is most probably because the mutations have modified a region that is involved in the interaction with factor H and hence have resulted in a reduced affinity for factor H.

EXAMPLE 8

A Site in C3 that can be Mutated to Modify the Interaction of C3i with Factor B

8.1 Introduction

The previous examples have demonstrated that mutations to C3 can modulate the interactions with factors H and I. In order to discover other sites in C3 that might interact with factor B, we compared the known sequences of C3 molecules from different species, as well as with available sequences for C4 and other homologous proteins. We identified the region corresponding to residues 1427–1433 of human C3 that might be involved in C3 and C4 specific functions. This could include interaction with factor B (or its homologue, C2, in the case of C4), but not necessarily because other potential functions include thiolester formation, conversion into C3b (or C4b form), interaction with substrate C3 and/or C5 in convertase activity and interaction with factor I and its cofactors. Therefore selected residues were mutated to the corresponding residues (based on sequence alignments) found in another homologous protein, in this case human C5. Thus residue 1427 was changed from an Arg to a Gln, residue 1431 from a Lys to Asp, and residue 1433 from a Glu to a Gln. The resulting mutant was found to be susceptible to cleavage by C3 convertase (CVFBb) and the C3b product was cleavable by factors H and I. However, this mutant did not support the conversion of factor B to Bb plus Ba, which is dependent on the binding of factor B to C3i (or C3b). Therefore we have evidence that mutation of this region has diminished the interaction with factor B. Whilst this is undesirable for the generation of a super-active C3 convertase, it does provide an indication that other modifications to this region of C3 will also alter the interaction with factor B, and some of these will probably increase the affinity. As a consequence such mutations may also increase the stability and activity of the bimolecular convertase enzyme, C3bBb (or C3iBb).

8.2 Methods

The alignments shown in Table 1 overleaf illustrate why we considered that this region was a candidate for mutagenesis. We surmised that characters of certain residues were well conserved in C3 and C4 but distinctly different in the other proteins. Residues 1427, 1431 and 1433 were selected because their charged nature might be indicative of groups involved in protein-protein interactions. The changes were made to the corresponding residues in human C5 because these displayed very different electrostatic properties, but within the context of some other conserved residues that might indicate a similar local structure.

TABLE I

Alignments of sequences of C3 and related molecules for region of residues 1427–1435 of human C3

| Protein | Species | RESIDUE (Human) | | | | | | | | |
| | | 1427 | 1428 | 1429 | 1430 | 1431 | 1432 | 1433 | 1434 | 1435 |
| --- | --- | --- | --- | --- | --- | --- | --- | --- | --- | --- |
| C3 | Human | R | Y | I | S | K | Y | E | L | D |
|  | Mouse | R | Y | I | S | K | Y | E | M | N |
|  | Rat | R | Y | I | S | K | Y | E | M | D |
|  | G. pig | R | Y | I | S | K | Y | E | L | D |
|  | Rabbit | R | Y | I | S | K | Y | E | L | N |
|  | Cobra | R | Y | I | S | K | F | E | I | D |
|  | Xenopus | K | Y | I | S | K | Y | E | V | N |
|  | Trout | R | Y | I | E | K | F | E | M | D |
| C4 | Human | R | Y | V | S | H | F | E | T | E |
|  | Mouse | R | Y | V | S | H | F | E | T | D |
| Slp | Mouse | R | Y | V | S | H | F | E | T | D |
| C3/C4-like | Hagfish | N | Y | I | V | Q | Y | E | I | R |
|  | Lamprey | K | Y | I | S | N | Y | E | I | T |

TABLE I-continued

Alignments of sequences of C3 and related molecules for region of residues 1427–1435 of human C3

| Protein | Species | RESIDUE (Human) | | | | | | | | |
|---|---|---|---|---|---|---|---|---|---|---|
| | | 1427 | 1428 | 1429 | 1430 | 1431 | 1432 | 1433 | 1434 | 1435 |
| C5 | Human | Q | L | F | T | D | Y | Q | I | K |
| | Mouse | Q | L | L | T | D | Y | Q | I | K |
| A2M | Human | P | T | V | K | M | L | E | R | S |
| | Mouse | P | S | V | K | R | L | Q | D | Q |
| | Rat | P | T | V | K | M | L | E | R | S |
| PZP | Human | P | T | V | K | M | L | E | R | S |
| Murinoglobulin | Mouse | P | T | V | K | K | L | E | R | L |
| A1M | Rat | P | S | V | K | K | L | Q | D | Q |
| A1M | G. Hamster | P | T | V | K | K | L | E | R | S |
| A1I3 | Rat | P | T | V | K | K | L | E | R | L |

The methods of mutagenesis, expression and analysis of C3 cleavage reactions were as described in the earlier examples (Examples 1–4). The mutagenic oligonucleotide was synthesised with the sequence: tggtgttgaccaatacatctc-cgactatcagctggacaa (SEQ ID NO: 12).

Assay for Turnover of Factor B

The expressed product was purified from the COS cell medium by affinity purification on a column of Clone-3-Sepharose as described in Example 9. This method results in considerable conversion of the thiolester broken form, C3i. Wild-type C3 was isolated by the same procedure. Dilutions of the wild-type C3 (1/5, 1/25 and 1/125) were run on an SDS-PAGE gel (reducing conditions) along with the mutant C3, and silver staining indicated that the mutant was present at a concentration equivalent to slightly less than the 1/25 but much more than the 1/125 dilution of wild-type. The same dilutions were used in the assay of factor B turnover. 5 μl of these C3's were incubated with 25 μl of CFD-G containing 5 μg/ml factor D and approximately 1.6 μg/ml of $^{125}$I-labelled factor B (approx. 1000–2000 dpm/μl) for 3 h at 37° C. The samples were then analysed by SDS-PAGE (reducing conditions) with autoradiography of the dried gel. The results are shown in FIG. 7.

8.3 Results

As shown in FIG. 7, distinct cleavage of factor B occurs even at a 1/125 dilution of the wild-type C3 (C3i). In contrast, no significant cleavage was observed in the presence of the mutant C3, even undiluted which should be at a concentration higher than the 1/125 sample of the wild-type.

This mutant therefore appears to have an impaired ability to support the cleavage of factor B, most likely due to a reduction in its binding affinity for factor B. Therefore this is a region of C3 that can be mutated to modulate the interaction between C3i (or C3b) and factor B and perhaps also the stability of the convertase (C3iBb or C3bBb).

EXAMPLE 9

Purification of Expressed Mutant C3 Molecules 9.1 Introduction

This example demonstrates how the mutant C3 molecules may be isolated from an expression medium, such as the culture medium of transfected eukaryotic cells. By simple affinity purification the C3 molecules are obtained in sufficient purity for functional tests and for conjugation to antibody by the method described in Example 10. Although elution from an antibody is accompanied by hydrolysis of a considerable proportion of the internal thiolester, the C3i product is still a suitable precursor for the generation of an active C3 convertase, as well as for the production of C3i-antibody conjugates. This approach is also likely to be useful as part of the preparation required for in vivo use.

9.2 Method

Affinity-purification on Clone-3-Sepharose

Clone-3 is a rat monoclonal antibody that is specific for C3 and its derivatives, including C3b and C3i (Lachmann, P. J. et al., 1980, *J. Immunol.* 41:503–515). Other monoclonal antibodies against C3 are available, and in some cases have been successfully used to isolate C3 from small quantities of human plasma (Dodds, A. W., 1993, *Methods Enzymol.* 223:46–61) and are therefore also likely to be applicable for the isolation of molecules expressed ex vivo. The IgG fraction was coupled to Sepharose CL-4B using cyanogen bromide (methodology may be found in Harrison and Lachmann, 1986, *Handbook of Experimental Immunology,* 4th edn., Ed.s Weir, Herzenberg, Blackwell and Herzenberg; Blackwell, Oxford). Culture supernatants were either passed directly through a column of this resin (re-circulated), or first concentrated by precipitation with 25% (w/v) Na$_2$SO$_4$, and resolubilization and dialysis into PBS, 5 mM NaN$_3$. The column is then washed successively with (i) PBS, 5 mM NaN$_3$ and (ii) PBS containing 1 M NaCl. Bound C3 elutes with 50 mM Na borate buffer, pH 10.5, and is immediately neutralised by collection of 0.9 ml fractions into 0.1 ml 1 M Tris/HCl pH 7. The material is then dialysed into PBS, 5 mM NaN$_3$.

Preparation of C3 Bearing a "His-Tag"

A "His-Tag" is a string of histidine residues that displays affinity for columns bearing Nickel ions. This method has been employed to aid the isolation of expressed proteins. We thought that this could be useful for the isolation of expressed mutant C3 molecules so we have used insertion mutagenesis to generate a plasmid encoding C3 with a tail of 6 histidine residues at the carboxy terminus (immediately carboxy-terminal to residue 1663). This location for the his tag was selected so as to minimise interference with the synthesis, folding, processing and disulphide bond formation of the nascent C3. Residue 1661 is a cysteine residue that is involved in a disulphide bond to a residue earlier in the sequence (probably Cys 1537; Dolmer, K. and Sottrup-Jensen, L., 1993, *FEBS-Lett* 315: 85–90) and therefore it seemed prudent to make the insertion beyond this structural feature. The mutation was introduced using the "gapped-plasmid" technique used in Example 1, using the mutagenic oligonucleotide synthesised with the sequence: tgggtgccccaaccatcatcatcatcatcattgaccacaccccc (SEQ ID NO: 13).

Incorporation of the correct sequence was confirmed by DNA sequencing. This DNA sequence may now be transferred to an expression vector. After transfection of eukaryotic cells, it should be possible to isolate the expressed C3 by affinity for a column bearing Nickel ions, or by any other matrix with specific affinity for the "His-Tag".

9.3 Results

A number of mutant C3 have been purified on the Clone-3-Sepharose, including those described in Examples 1 and 2 expressed in CHO cells. The products retained the ability to support the cleavage of factor B by factor D. The same method was used to isolate the mutant described in Example B2, expressed in COS cells. Silver-staining of SDS-PAGE gels indicated that the isolated products were not 100% pure, but often appeared to be greater than or equal to 50% pure. This comes from starting materials generally containing less than 10 µg/ml C3 in 10% (v/v) fetal calf serum plus other cellular proteins. In addition the C3's were not degraded during isolation, and endogenous factor H and I activity appeared to have been removed.

Purification by virtue of the "His-Tag" involves milder elution conditions from a column bearing Nickel ions. For example, EDTA has been used. Application of this method to C3 should therefore allow isolation without rupture of the internal thiolester bond.

EXAMPLE 10

Conjugation of C3i to Antibody and Use to Target C3 Convertase Activity Against a Particular Cell 10.1 Introduction One aspect of the invention is that stable C3 convertases derived from mutant C3 molecules will cause enhanced C3 conversion which, if localised at a particular target site, will promote complement-dependent attack of that target. The favoured approach for targeting the response is to couple the mutant C3 molecule, as either the C3i or C3b derivative, to an antibody specific for the desired target. In this example we demonstrate a working methodology for formation of such conjugates, which is applicable to mutant C3i or C3b molecules and can be used on material affinity-purified from an expression system, even if the thiolester of C3 has been broken in the process. By coupling C3i to an antibody that specifically binds to sheep erythrocytes, we further show that the the conjugate fixes C3i to the erythrocyte surface such that a convertase, C3iBbP, can be formed that initiates lysis of these cells when other complement components are supplied in the form of normal guinea-pig serum (in EDTA to prevent de-novo formation of C3 convertases). Hence conjugation to antibody can be used to target a C3i molecule to initiate complement-dependent attack of a particular cell type. This example uses wild-type C3i, from human plasma, that forma a C3 convertase in vitro. In vivo, wild-type C3i and C3b are broken down by factor H and I. Therefore a mutant C3, constructed according to the plans in this patent to be resistant to factors H and I and therefore forming a stable C3 convertase, would be advantageous in a physiological context.

10.2 Method (i) Generation and Purification of C3i-antibody Conjugate

The antibody used was the IgG fraction isolated from a polyclonal rabbit anti-sheep erythrocyte antiserum. 1.1 mg was incubated with 75 nmol of SPDP in conjugation buffer, pH 7.5 (20 mM $KH_2PO_4$, 60 mM $Na_2HPO_4$, 0.12 M NaCl) for 2 h at room temperature. The PDP-IgG was purified by gel-filtration on a Superose-6 column (Pharmacia) (in a phosphate buffer, pH 7.4, containing 0.5 M NaCl). Reduction of a sample with dithiothreitol was used to estimate 4 PDP groups coupled per molecule of IgG. C3i was prepared by treatment of purified C3 with 0.1 M methylamine, pH 7.2 (2 h at 37° C.). Excess methylamine was removed by gel-filtration followed by dialysis into conjugation buffer. 18 nmole of C3i was mixed with 1.7 nmoles of PDP-IgG in 1.26 ml conjugation buffer and incubated for 1 day at room temperature followed by 1.5 days at 4° C. FIG. 8 shows a Coomassie Blue stained SDS-PAGE gel of the conjugation reaction mixture showing the appearance of a species of approximately 350 kDa that was not present in either PDP-IgG or C3i. This species was partially purified by gel-filtration on the Superose-6 column in a phosphate buffer, pH 7.4, containing 0.5 M NaCl and then dialysed into PBS. It eluted before the C3, in a volume from which a molecular weight of 300–400 kDa could be estimated by calibration with globular molecular weight standards. Concentrations of conjugate, free antibody and uncoupled C3 were estimated from a Coomassie-stained SDS-PAGE gel (non-reducing conditions). Two-dimensional SDS-PAGE (first dimension unreduced, second dimension reduced) revealed a pattern compatible with a 1:1 conjugate between IgG and C3i.

(ii) Demonstration that the C3-antibody Conjugate can be Used to Target Convertase Activity Against a Particular Cell 20 µl of dilutions of the conjugate (0 (no conjugate), 1/100, 1/50, 1/10) were incubated with 100 µl of approximately 1% (v/v) sheep erythrocytes (prewashed in CFD) for 1 hour at 37° C. Parallel incubations were performed with equivalent amounts of PDP-IgG (no C3) and C3 alone. The cells were then washed 4 times in CFD and resuspended to 100 µl in CFD-G. 50 µl of this were lysed with 150 µl $H_2O$, followed by addition of 800 µl of CFD containing 10 mM EDTA and 2% (v/v) NGPS. The other 50 µl of conjugate-coated cells were incubated for 15 min at 37° C. with 50 µl of CFD-G containing 190 µg/ml factor B, 2 µg/ml factor D, 20 µg/ml properdin and 0.6 mM $NiCl_2$, followed by lysis with 900 µl of CFD containing 10 mM EDTA and 2% (v/v) NGPS. After 30 min at 37° C., the cells were pelleted by centrifugation (2000×g, about 3 min) and the optical absorbance of the supernatant was measured at 412 nm. Using the $H_2O$-treated samples as 100% lysis, and a buffer blank devoid of cells, the % lysis was calculated, as shown in FIG. 9. The conjugate produced dose-dependent lysis, whereas neither the PDP-IgG nor the C3i alone generated any lysis significantly above that observed in the absence of any such treatment.

10.3 Summary of Results

The method used has proved successful for coupling C3i to IgG as shown by:

1. The formation of a band of appropriate size (about 350 kDa) for a 1:1 C3:IgG conjugate shown by SDS-PAGE in FIG. 8.
2. Two-dimensional SDS-PAGE (first dimension non-reduced, second dimension reduced) indicated that this species contained both IgG and C3i.
3. The elution characteristic of this species on gel-filtration is again consistent with a molecule of about 350 kDa.
4. The conjugate displays a haemolytic activity that is not displayed by either PDP-IgG or C3i (FIG. 9).

The haemolytic assay (FIG. 9) further demonstrates that:

1. The specific anti-sheep erythrocyte antibody has localised the C3i to the target cell (sheep erythrocyte) membrane, preventing it from being removed by washing (in contrast to free C3i).
2. The conjugate retains the activity of the C3i in that it is still able to form a C3 convertase by reaction with properdin and factors B and D.
3. This convertase can initiate complement-dependent attack of the target, in this case by activating the lytic pathway (C5-9) to lyse the erythrocyte.

Additional data from other laboratories show that cobra venom factor can be coupled to an antibody and that these conjugates can target complement activation against a particular cell type (Vogel, 1988, *Targeted. Diagn. Ther.,* 1:191–224; Muller, B. and Muller-Ruchholtz, W., 1987, *Leuk. Res.* 11:461–468; Parker, C. J., White, V. F. and Falk, R. J., 1986, *Complement* 3:223–235; Petrella, E. C. et al, 1987, *J. Immunol. Methods* 104:159–172). These data support the contention that C3 modified so that it is capable of forming a stable C3 convertase, like cobra venom factor, could be used to target complement-mediated responses, as outlined in this invention.

EXAMPLE 1

Demonstration that Mutant C3 Molecules Induce Factor B Turnover in Normal Human Serum 11.1 Introduction A major purpose of the invention described herein is the consumptive depletion of complement activity from biological fluids. The invention describes methods for the manufacture of C3 molecules that are resistant to down-regulation by factors H and I. In this state they will bind factor B and generate active C3 convertases. The activity of these convertases is demonstrated by the haemolytic assay employed in Example 6. Such a convertase will therefore consume C3. If the convertase is unstable, it will dissociate without much C3 conversion. However this will allow binding of fresh factor B, and its conversion to Bb and Ba. Thus the mutant C3 will promote the consumption of factor B, leading ultimately to the disablement of the alternative pathway, and its inability to amplify classical pathway stimulation. If a stable C3 convertase is formed, turnover of factor B will be reduced, but consumption of C3 will be increased. Both situations can therefore be desirable. In this example we demonstrate that mutant C3 molecules that are modified to make them resistant to factor I, but without any modification to modify the stability of the convertase, promote accelerated turnover of factor B in human serum. Wild-type C3, in contrast, causes no significant turn-over, presumably because wild-type C3i is rapidly degraded by factors H and I.

1.2 Method

The Mutants prepared are as follows:

Q1R2 Arg1303 changed to Gln (Example 2)

Q1Q2 Arg1303 changed to Gln, plus Arg1320 changed to Gln (Example 1)

E1Q2 Arg1303 changed to Glu, plus Arg1320 changed to Gln (Example 5)

These mutants were all expressed in CHO cells and then purified by precipitation with $Na_2SO_4$, followed by affinity purification on Clone-3-Sepharose, as described in Example B3. Wild-type C3 (R1R2) was similarly isolated. By SDS-PAGE with silver-staining, the concentration of Q1 was between 1/5 and 1/25 of the wild-type, the concentration of Q1Q2 was about that of 1/5 wild-type, and the concentration of E1Q2 was between 1/25 and 1/125 of wild-type. All preparations probably contained a majority of thiolester-broken molecules (C3i).

10 µl of these C3 preparations were incubated with 10 µl of a solution of 20% (v/v) normal human serum in PBS containing 1 mM $MgCl_2$ and approximately 300 ng $^{125}$I-labelled factor B (approx. 2–300,000 dpm) for 1 hour at 37° C. 5 µl was then analysed by SDS-PAGE (reducing conditions). The dried gel was exposed to autoradiography film to indicate the positions of the bands corresponding to the intact factor B and its cleavage products. These were then excised and counted to accurately determine the degree of cleavage. The value obtained in buffer alone was subtracted as background (encompassing not only background cleavage, but also degradation products and other impurities present in the radioligand preparation).

11.3 Results

The resulting degrees of factor B cleavage are shown below:

| | |
|---|---|
| 1/25 Wild-type | 1.49% |
| 1/5 Wild-type | 2.74% |
| Q1R2 | 6.19% |
| Q1Q2 | 7.41% |
| E1Q2 | 6.42% |

Therefore the factor I resistant mutants all produce greater levels of factor B cleavage than equivalent amounts of wild-type C3 (C3i). With larger doses or longer incubations, complete incapacitation of the alternative pathway should result.

The abbreviations used in the foregoing examples include: CFD, complement fixation diluent (defined in Harrison and Lachmann, 1986, *Handbook of Experimental Immunology,* 4th edn., Ed.s Weir, Herzenberg, Blackwell and Herzernerg; Blackwell, Oxford); CFD-G, CFD containing 0.1% (w/v) gelatin; PBS, phosphate-buffered saline; NGPS, normal guinea-pig serum; SDS-PAGE, SDS-polyacrylamide gel electrophoresis; SPDP, N-Succinimidyl-3-[2-pyridyldithio]propionate.

EXAMPLE 12

Mutation of Residues 992–1000

1. Introduction

Other laboratories have produced evidence based on the effects of synthetic peptides (Ganu, V. S. and Muller-Eberhard, H. J., 1985, Complement 2:27; Becherer, J. D. et al., 1992, Biochemistry 31:1787–1794; Fishelson, Z., 1991, Molecular Immunology 28:545–552; Lambris, J. D., Ganu, V. S., Hirani, S. and Muller-Eberhard, H. J., 1988, J. Biol. Chem. 263;12147–12150) to suggest various residues in human C3b that might be involved in the interaction with Factor H. We have used the different approach of sequence comparison to predict residues involved in C3-specific functions. Site-directed mutagenesis has been performed and has indicated that most of these candidates have little or no influence on the functional susceptibility to Factor H. However, a few mutations did reduce the susceptibility to Factor H. These mutations were made to parts of the molecule that have not previously been identified as interacting with Factor H or modulating its binding. Hence mutagenesis of these defined residues can be used to produce mutant derivatives of C3 that are partially or completely resistant to inhibition by Factor H within a physiological environment, and will form complex C3 convertase enzymes (C3bBb etc) that are similarly resistant to inactivation by Factor H.

Factor H is structurally homologous to other complement inhibitory proteins, including CR1, MCP and DAF. In view of this apparent evolutionary relationship, and mutual competition for binding, it is likely that they interact with C3b in a structurally similar manner to Factor H (Farries et al., 1990, Complement Inflamm. 7:30–41). Therefore the mutations described which modulate the suspectibility to Factor H are also likely to be useful for modulating the interactions with these other proteins, especially for the purpose of evading their complement down-regulatory activities. They may also find application for the modification of the interaction with the SCR domains in Factor B (and the homologous domains in C2 involved in binding to C4b). Mutations to the corresponding regions of C4 and C5 might also be useful to modify their interactions with the SCR domains in C1r and C1s (C4), C4b-binding protein (C4b), and C6 and C7 (C5b).

2. Method 2.1 Searching for Residues Involved in C3-specific Functions.

These predictions were made from alignments of human C3 with all the homologous proteins for which sequences were available through public data bases. These included the functionally equivalent molecules in mouse, rat, guinea-pig, rabbit, cobra, xenopus, chicken and trout, human and mouse C4, human and mouse C5, C3-like proteins from lamprey and hagfish, cobra venom factor (CVF), and human alpha-2-macroglobulin and its homologues. Searches were then made for residues that were conserved among different C3s, but distinctly different in homologues (notably C5 and CVF) that lack the C3-specific functions of interest. Some of these have been mutated to encode the corresponding residues in C5 or CVF, expressed in COS cells and the secreted products tested for cleavage in the presence of CVFBb and Factor H and I. All methods are as described in the standard methods and example 1. A summary of the results is shown in Table II.

2.2 Construction and Analysis of Mutant DV-1AM

This mutant was made in the same way as the other mutants, using the "megaprimer method" as described by V. Picard et al., 1994, *Nuc. Acid. Res.* 22:2587–2591. The mutagenic primer had the sequence ccagatgacaagtgctgccgt-cagccagtcagggctgaagcacc (SEQ ID NO: 14) encoding the mutations E992S, D993A, D996S, A997Q, E998S and R999G. The up-stream primer had the sequence tgtcatcgt-gccgctaaaga (SEQ ID NO: 15) (corresponding to deoxynucleotides 2754–2773), and the down-stream primer had the sequence gttttatggtgaccttaaggtcgaatttatta (SEQ ID NO: 7) (complementary to deoxynucleotides 4130–4165, with the introduction of a cleavage site for the restriction enzyme Afl II at position 4149) The mutated DNA fragment was ligated into a vector that contained the coding sequence for C3 also with the introduced site for Afl II at position 4149, by cutting both pieces with Afl II and EcoRI (cuts at position 2997), purifying the desired products and ligating together using T4 DNA ligase. Plasmid DNA was isolated from transformed bacterial colonies, and genuine mutants identified by DNA sequencing. At this point it was found that the DNA sequence had been additionally mutated to encode the mutation L1000M. The resulting expression vector was transfected into COS cells, and the secreted expressed product analysed for cleavage reactions as previously described.

3. Properties of Mutant DV-1AM

Analysis of the expressed product with the DV-1AM mutations is shown in FIG. 10 The points to note are:

(i) The western blot is developed with monoclonal antibodies to the C3dg region of C3 that detect the precursor, alpha, alpha', 77 and 68 kDa fragments, but not the beta, 43 or 46 kDa fragments.

(ii) All bands of the DV-1AM product (lanes B1-4) appear slightly below the equivalent wild-type bands (lanes A1-4). The shift in mobility is a consequence of the mutations made.

(iii) Cleavage of wild-type C3 with CVFBb produces some alpha' chain from C3b, but a larger amount of 68 kDa fragment resulting from cleavage of the C3b to iC3b by endogenous Factor H and I activity (lane A3). Addition of exogenous H and I completes the conversion of C3b to iC3b (lane A4). In contrast, cleavage of the DV-1AM product by CVFBb produces a larger amount of alpha' chain and only a small amount of 68 kDa fragment (lane B3). Addition of exogenous H and I then converts this C3b into iC3b (lane B4). Therefore the mutant C3b is much more resistant than the wild-type to endogenous H and I, although resistance is not complete as indicated by susceptibility to cleavage by high concentrations of exogenously added H and I.

4. Conclusion

The DV-1AM mutation creates resistance to Factor H-dependent cleavage by Factor I. The mechanism is not certain, although because the modified residues are far (in the primary structure) from the sites of cleavage by Factor I, it is likely that it is the interaction with Factor H that is impaired. In this case the mutation will also impart resistance to the other inhibitory activities of Factor H, namely:—(i) competition with Factor B for binding to C3b (or C3i), and (ii) accelerated dissociation of the C3bBb and C3bBbP convertases. The DV-1AM mutation has modified residues either directly or indirectly involved in maintaining the affinity for Factor H. Many different mutations of the same residues will presumably have similar effects, and mutation of only some of the residues modified here, as well as other residues within this segment of the primary structure, is also likely to achieve such an effect.

EXAMPLE 13

Mutation of Residues 1001–1005

1. Introduction

As described in the above example, the residues 1001, 1002 and 1005 were also identified as candidates that might be essential for C3-specific functions. Mutation confirms that modification of these residues can be used to impart resistance to Factor H.

2. Method 2.1 Construction and Analysis of Mutant DV-1B

The method used was as described for the preceding example, with the exception that the mutagenic primer had the sequence aacggctgaacatattaattcataccccctcgggc encoding the mutations K1001N, H1002I and V1005H. Sequence analysis of isolated plasmid DNA confirmed that the correct mutation had been introduced. No other mutations were detected.

3. Properties of Mutant DV-1B

Analysis of the expressed product with the DV-1B mutations is shown in FIG. 11. The points to note are:

(i) The western blot is developed with a polyclonal antibody to the C3 that detects the precursor, alpha, alpha', beta, 43 and 46 kDa fragments strongly, and only weakly detects the 77 and 68 kDa fragments. Note that the alpha and alpha' chains are not transferred and detected with 100% efficiency, so the intensity of these bands is less than expected and a poor guide to the actual amounts present.

(ii) Cleavage of wild-type C3 with CVFBb produces a small amount of alpha' chain from C3b, but most of this is lost due to cleavage of the C3b to iC3b by endogenous Factor H and I activity (lane B3). This appears mostly as 43 kDa fragment, although a small amount of the 46 kDa intermediate is visible. Addition or 2 μg/ml exogenous H (lane B4), with Factor I, causes marked further cleavage and 10–50 μg/ml exogenous H (lanes B5, B6) completes the conversion of C3b to fully cleaved (no alpha' or 46 kDa bands) iC3b. Cleavage of the DV-1B product by CVFBb also produces a small amount of alpha' chain (lane A3; the total amount of C3 present is much less, and the alpha and alpha' bands are very faint). Significantly, the amount of 43 kDa chain generated in the absence of exogenous H and I is less than in the wild-type, and the appearance of the 46 kDa intermediate fragment is relatively greater, indicating less effective cleavage. Addition of exogenous H and I (lanes A4–6) completes the conversion of this C3b into iC3b, but the 43 kDa product is seen to increase dose-dependently upto 50 μg/ml H (lane A6), when the 46 kDa intermediate is still evident. Therefore the mutant C3b is more resistant than the wild-type to endogenous and exogenous H and I, although resistance is not complete as indicated by susceptibility to cleavage by high concentrations of exogenously added H and I.

4. Conclusion

The DV-1B mutation creates resistance to Factor H-dependent cleavage by Factor I. The mechanism is not certain, although because the modified residues are far (in the primary structure) from the sites of cleavage by Factor I, and the effect was dependent on the dose of Factor H added, it is likely that it is the interaction with Factor H that is impaired. In this case the mutation will also impart resistance to the other inhibitory activities of Factor H, namely:—(i) competition with Factor B for binding to C3b (or C3i), and (ii) accelerated dissociation of the C3bBb and C3bBbP convertases. The DV-1B mutation has modified residues either directly or indirectly involved in maintaining the affinity for Factor H. Many different mutations of the same residues will presumably have similar effects, and mutation of only some of the residues modified here, as well as other residues within this segment of the primary structure, is also likely to achieve such an effect.

EXAMPLE 14

Mutation of Residues 1152–1155

1. Introduction

As described in the above examples, the residues 1152, 1153 and 1155 were also identified as candidates that might be essential for C3-specific functions. Mutation confirms that modification of these residues can be used to impart resistance to Factor H.

2. Method 2.1 Construction and Analysis of Mutant DV-6

The method used was as described for the preceding example, with the exception that the mutagenic primer had the sequence atctcgctgcgcaaggctttcgatatttgcgag (SEQ ID NO: 18)encoding the mutations Q1152R, E1153K and K1155F. Sequence analysis of isolated plasmid DNA confirmed that the correct mutation had been introduced. No other mutations were detected.

3. Properties of Mutant DV-6

Analysis of the expressed product with the DV-6 mutations is shown in FIG. 11. The points to note are:

(i) As described in the preceding example, the western blot is developed with a polyclonal antibody to the C3 that detects the precursor, alpha, alpha', beta, 43 and 46 kDa fragments strongly, and only weakly detects the 77 and 68 kDa fragments. Note that the alpha and alpha' chains are not transferred and detected with 100% efficiency, so the intensity of these bands is less than expected and a poor guide to the actual amounts present.

(ii) Cleavage of wild-type C3 with CVFBb produces a small amount of alpha' chain from C3b, but most of this is lost due to cleavage of the C3b to iC3b by endogenous Factor H and I activity (lane B3). This appears mostly as 43 kDa fragment, although a small amount of the 46 kDa intermediate is visible. Addition of 2 μg/ml exogenous H (lane B4), with Factor I, causes marked further cleavage and 10–50 μg/ml exogenous H (lanes B5, B6) completes the conversion of C3b to fully cleaved (no alpha' or 46 kDa bands) iC3b. Cleavage of the DV-6 product by CVFBb also produces a small amount of alpha' chain (lane C3). Significantly, the amount of 43 kDa chain generated in the absence of exogenous H and I is less than in the wild-type, and the amount of 46 kDa intermediate is relatively greater, indicating less effective cleavage. Addition of exogenous H and I (lane C4-6) completes the conversion of this C3b into iC3b. However, whereas with the wild-type the 46 kDa intermediate was eliminated by 10 μg/ml H (lane B5), indicating complete cleavage, this species still persisted with the mutant with H at this concentration (lane C5), and complete cleavage was only apparent when 50 μg/ml H was used. Therefore the mutant C3b is more resistant than the wild-type to endogenous H and I, although resistance is not complete as indicated by susceptibility to cleavage by the highest concentrations of exogenously added H and I.

4. Conclusion

The DV-6 mutation creates resistance to Factor H-dependent cleavage by Factor I. The mechanism is not certain, although because the modified residues are far (in the primary structure) from the sites of cleavage by Factor I, and the effect was dependent on the dose of Factor H added, it is likely that it is the interaction with Factor H that is impaired. In this case the mutation will also impart resistance to the other inhibitory activities of Factor H, namely:—(i) competition with Factor B for binding to C3b (or C3i), and (ii) accelerated dissociation of the C3bBb and C3bBbP convertases. The DV-6 mutation has modified residues either directly or indirectly involved in maintaining the affinity for Factor H. Many different mutations of the same residues will presumably have similar effects, and mutation of only some of the residues modified here, as well as other residues within this segment of the primary structure, is also likely to achieve such an effect.

TABLE II

SUMMARY OF EFFECTS OF MUTATIONS ON SUSCEPTIBILITY TO FACTOR H

| Mutation | Amino Acid Changes | Inhibition of Factor H dependent cleavage by Factor I |
|---|---|---|
| CV-2 | E776K | – |
| CV-1 | P963K, P964A, A965R, D966K | – |
| DV-1AM | E992S, D993A, D996S, A997Q, E998S, R999G, L1000M | ++ |
| DV-1B | K1001N, H1002I, V1005H | + |
| DV-3 | T1031G, E1032N, Q1033H, E1035N, K1036I | – |
| DV-4 | V1070K, K1071G, R1072G, A1073S, P1074A | – |
| CV-5 | R1134Q | – |
| DV-6 | Q1152R, E1153K, K1155F | + |
| DV-7N | D1174N | – |
| DV-9 | D1216G, K1217E, N1218D, R1219H | – |
| CV-4 | R1260N, G1264E | – |
| RY-1 | R1427Q, K1431D, E1433Q | – |

Key:
–, no inhibition detected;
+, small inhibition;
++, larger inhibitory effect

EXAMPLE 15

Alteration of Residues 1546–1663

1. Introduction

Unlike previous examples (12–14) modification of residues 1546–1663 was not based on consideration of sequence comparisons between C3 and related proteins. Instead the modification described was created by accident, a consequence of an unintended nucleotide deletion that caused a frame-shift in the translation of the C-terminal residues. The resulting product displayed considerable resistance to Factor H-dependent cleavage by Factor I. Therefore similar modifications created by design are likely to be useful for conferring resistance to the regulatory actions of Factor H and/or Factor I.

2. Method

A vector equivalent to NC3, but carrying additional mutations to 3151g, 3152g, 3154a, 3156c, 3159c, 3163a, 3165t, 3167t, 3168t that translate into the amino acid changes T1031G, E1032N, Q1033H, E1035N and K1036I was digested with restriction enzymes Pvu I (cuts in vector sentence) and BsrG I (cuts at nucleotide 4692), and the 6.1 kb band isolated by agarose gel electrophoresis. Another vector equivalent to NC3 but carrying the insertion of catcatcatcatcatcat (SEQ ID NO: 25) after nucleotide 5049, to encode the insertion of amino acids HHHHHH (SEQ ID NO: 26) at the C-terminus, was similarly digested with Pvu I and BsrG I, and the 4.4 kb fragment isolated. These two DNA fragments were ligated together, and a complete plasmid was isolated. DNA sequencing found that a single nucleotide (a4696 or a4697) had been lost. The predicted consequence is that amino acids 1546–1663 cannot be translated in frame. Instead, there will be 48 residues read out of the normal fame until a stop codon is reached.

The product, "HDV-3X", was expressed in COS cells and tested as described in the preceding examples.

3. Properties of Mutant HDV-3X

Analysis of the expressed product with the HDV-3X modification is shown in FIG. 12. The points to note are:

(i) The western blot is developed with monoclonal antibodies to the C3dg region of C3 that detect the precursor, alpha, alpha', 77 and 68 kDa fragments, but not the beta, 43 or 46 kDa fragments.

(ii) HDV-3X is compared with mutant DV-3, as the equivalent product without the additional C-terminal modification. The HDV-3X displays a smaller alpha chain, but normal sized 68 kDa and 77 kDa products, consistent with a truncation at the C-terminus.

(iii) Cleavage of DV-3 C3 with CVFBb in the presence of Factor I produces some alpha' chain from C3b, but a larger amount of 68 kDa fragment resulting from cleavage of the C3b to iC3b dependent on endogenous Factor H (lane A2). Addition of exogenous H completes the conversion of C3b to iC3b (lane A3-5). The conversion is virtually complete with only 1 µg/ml Factor H (lane A3). In contrast, cleavage of the HDV-3X product by CVFBb produces a larger amount of alpha' chain and only a small amount of 68 kDa fragment (lane B2) Addition of exogenous H is ineffective in converting this C3b into iC3b (lane B3-5). Only slight formation of 68 kDa and 77 kDa products is detectable even with 25 µg/ml H (lane A5). Therefore the HDV-3X C3b is much more resistant than the wild-type to endogenous H and I. The fact that resistance is partially overcome by higher amounts of Factor H suggests that the affinity for Factor H may be greatly reduced.

4. Conclusion

The HDV-3X modification creates resistance to Factor H-dependent cleavage by Factor I. The mechanism is not certain, although because the modified residues are far (in the primary structure) from the sites of cleavage by Factor I, it is likely that it is the interaction with Factor H that is impaired. In this case the mutation will probably also impart resistance to the other inhibitory activities of Factor H, namely:—(i) competition with Factor B for binding to C3b (or C3i), and (ii) accelerated dissociation of the C3bBb and C3bBbP convertases. The HDV-3X modification has affected residues either directly or indirectly involved in maintaining the affinity for Factor H. Many different deletions or mutations of the same residues will presumably have similar effects, and deletion or mutation of only some of the residues modified here is also likely to achieve such an effect.

The HDV-3X modification was not created by design. But the methods of choice for creating this and related modifications are likely to be specific methods of site-directed mutagenesis, including those methods described in preceding examples.

EXAMPLE 16

Modification of Residues 954 and 955 to Prevent Factor I Mediated Cleavage at this Site 1. Introduction Previous mutagenesis at the $P_1$ residues (1303 and 1320) provided resistance to cleavage by Factor I at the first two sites (examples 1–6). It was not known if prevention of cleavage at these two sites would also prevent cleavage at a third site responsible for release of C3c from C3dg. This third cleavage, which is normally dependent on CR1 (a membrane bound receptor that has been engineered into a soluble form, sCR1) as a cofactor, is relatively slow and has only previously been observed on iC3b (or iC3i) (i.e. after cleavage at sites 1 and 2) and not on C3i or C3b. To test this, the E1Q2 mutant (described in example 11), which is highly resistant to cleavage at sites 1 and 2, was used. If this mutant was still susceptible to cleavage at site 3, it would indicate that it would be desirable to mutate this site to prevent degradation of the molecule in physiological fluids. However, there are conflicting reports in the literature as to whether the cleavage occurs exclusively at the 954–955 bond (Davis, A. E. 3d. Harrison, R. A. & Lachmann, P. J., 1984, *J. Immunol.*, 132:1960–6), or whether cleavage can also occur at other positions, such as 959–960 (Harrison, R. A. et al., 1996 *Molecular Immunology* 33, Suppl. 1, 59, abstract 235; Ekdahl, K. N., Nilsson, U. R. & Nilsson, B., 1990, *J. Immunol.* 144: 4269–74). Initially we mutated residue 954 from arginine to Glutamic acid (to make E1Q2E3) because (i) this appears from the above publications to be the P1 residue of one of the cleavage sites, and (ii) from example 5 at site 1, where mutation to Glutamic acid imparted higher resistance to cleavage than other substitutions. In addition other mammalian species (mouse, rat, guinea pig, rabbit) of C3 have Glutamine and Glycine at the residues equivalent to 954 and 955, instead of the arginine and Glutamic acid of human C3 (e.g. Mavroidis, M., Sunyer, J. O. & Lambris, J. D., 1995, *J. Immunol.* 154:2164–2174). These data suggest that this site (954–955) would not be well cleaved in other species, and that another site, such as 959–960, might be more important (Harrison, R. A., et al., 1996, *Molecular Immunology* 33, Suppl. 1, 59, abstract 235). The equivalent mutations of arg954 to Gln, and Glu955 to Gly were therefore made to human C3 to make the E1Q2QG3 mutant.

2. Method

The method used for mutant construction was as described for preceding examples, with the exception that the mutagenic primer for the E1Q2E3 mutant had the sequence gaacgcctgggcgaagaaggagtgcag (SEQ ID NO: 19) encoding the mutation R954E, and the mutagenic primer for the E1Q2QG3 mutant had the sequence aacgcctgggccaaggaggagtgcagaa (SEQ ID NO: 20) encoding the mutations R954Q, E955G. The product was ligated into a construct that contained the mutations encoding E1Q2 (E1303, Q1320, as described in examples 5 and 11). Sequence analysis of isolated plasmid DNA confirmed that the correct mutation had been introduced. No other mutations were detected. The resulting expression vectors were transfected into COS cells, and the secreted expressed product analysed for cleavage reactions as previously described.

3. Factor I-mediated Cleavages of E1Q2, E1Q2E3 and E1Q2QG3 Mutants

Analysis of the expressed products is shown in FIG. 13. The points to note are:
(i) The western blot is developed with monoclonal antibodies to the C3dg region of C3 that detect the precursor, alpha, alpha', 77 and 68 kDa fragments, but not the beta, 43 or 46 kDa fragments. In addition the 86 kDa product of cleavage at site 3, without cleavage at sites 1 or 2, will be detected.
(ii) The figure shows that the 86 kDa product is indeed formed by Factor I-mediated cleavage of E1Q2 in the presence of sCR1 (lane A3), but not when Factor H is the cofactor (lane A2).
(iii) The 86 kDa product is not formed in either of the E1Q2E3 (C) or E1Q2QG3 (B) mutants, even in the presence of sCR1 (C3 and B3).

4. Conclusion (i) Factor I-mediated cleavage at site 3 can still occur when cleavage at sites 1 and 2 have been blocked. Therefore additional blockage of cleavage at site 3 is desirable to prevent degradation of any mutant product that is otherwise only resistant at sites 1 and 2, when used in a physiological environment.

(ii) Cleavage at site 3 can be blocked by mutation of residue 954 to Glu, and by mutation of 954 and 955 to Gln and Gly. Therefore other mutations of residues 954 and/or 955 are also likely to impart resistance to cleavage at site 3.

(iii) The mutations shown did not allow cleavage at other putative positions of third site cleavage (such as 959–960), even though such sites were not mutated. This would indicate that either 954–955 is the only significant site of cleavage, or that other cleavages require prior cleavage at 954–955, or that mutation of these residues prevents cleavage at other positions by a different mechanism (such as conformational distortion). In any case, mutations of 954 and/or 955 are effective means of preventing degradation of C3b or C3i-like products.

EXAMPLE 17

Modifications to the Carboxy-terminal Region of C3 that Inhibit Cleavage by Factor I 1. Introduction Example 15 provided evidence that mutation or deletion of residues 1546–1663 imparted resistance to cleavage by Factor I. This example provides further smaller scale mutants that also impart this resistance, as well as various mutations that do not.

2. Method

The method used for mutant construction was as described for preceding examples, with the exception that the mutagenic primers had the sequences shown in table III, encoding the mutations indicated. Sequence analysis of isolated plasmid DNA confirmed that the correct mutation had been introduced. No other mutations were detected. The resulting expression vectors were transfected into COS cells, and the secreted expressed product analysed for cleavage reactions as previously described.

3. Resistance of Various Mutants to Cleavage by Factor I

The results of cleavage assays performed with Factors I and H on these mutants are shown in FIGS. 14 and 15. Note that the western blots are developed with monoclonal antibodies to the C3dg region of C3 that detect the precursor, alpha, alpha', 77 and 68 kDa fragments, but not the beta, 43 or 46 kDa fragments.

FIG. 14 shows that the wild-type (NC3,A), FT-3(D), FT-4(E) and FT-5(F) products are cleaved by Factor I, as indicated by the appearance of 77 kDa and/or 68 kDa bands and the disappearance of the alpha chain. In contrast FT-1 and FT-2 are not cleaved.

FIG. 15 shows that the wild-type (NC3,A), FR-1(B), FR-2(C), FR-3(D) and FR-4(E) products are cleaved, while again the FT-2 product (F) is cleaved.

4. Conclusions (i) Even the small truncation of FT-2 is sufficient to impart resistance to cleavage by Factor I. Such resistance can therefore be achieved by deletion of some or all of residues 1636–1663. This conclusion is supported by the resistance displayed by FT-1 which includes deletion of residues 1636–1663, with additional deletion/modification of residues 1591–1635.

(ii) As residues 1636–1663 are required for Factor I-mediated cleavage, many other modifications of these residues are likely to generate resistance.

(iii) Not all modifications of these residues impart resistance. Ineffective modifications include those defined by FT-5, FR-1, FR-2, FR-3 and FR-4, as well as the modifications defined by FT-3 and FT-4 that modify residues other than 1636–1663.

(iv) These data imply that the residues within 1636–1663 that are required for cleavage are those that have not been modified by FT-5, FR-1, FR-2, FR-3 or FR-4. Therefore some of the residues 1649–1660 may be critical.

TABLE III

MUTANTS USED IN EXAMPLE 17

| Mutant | Sequence of mutagenic primer | Sequence replaced | Residues | Replaced by |
|---|---|---|---|---|
| FT-1 | | REA | 1591–1593 | TN stop |
| FT-2 | | E | 1636 | stop |
| FT-3 | | LSSDFWGE (SEQ ID NO:27) | 1607–1614 | KEALQI (SEQ ID NO:28) |
| FT-4 | | IIGKD (SEQ ID NO:29) | 1621–1625 | RYIYPLDSL (SEQ ID NO:30) |
| FT-5 | | C | 1661 | S |
| FR-1 | | EEDE (SEQ ID NO:31) | 1633–1636 | RDTT (SEQ ID NO:32) |

TABLE III-continued

MUTANTS USED IN EXAMPLE 17

| Mutant | Sequence of mutagenic primer | Sequence replaced | Residues | Replaced by |
|---|---|---|---|---|
| FR-2 | | QDEENQKQ (SEQ ID NO:33) | 1638–1645 | SS |
| FR-3 | | QDEENQKQ (SEQ ID NO:33) | 1638–1645 | RSTRQRAA (SEQ ID NO:34) |
| FR-4 | | D | 1648 | AFLAN (SEQ ID NO:35) |

References:
1. Bergmann, M. & Fruton, J. S. (1941) *Adv. Enzymol.*, 1:63–98.
2. de Bruijn, M. H. & Fey, G. H. (1985), *Proc. Natl. Acad. Sci. U.S.A.* 82:708–712.
3. Crawford-M H et al. (1988) *Circulation*. 78:1449–58.
4. Daha, M. R. & van Es, L. A. (1982) *Immunol*. 43:33–38.
5. Farries, T C; Lachmann, P J & Harrison, R A (1988) *Biochem. J.* 252:47–54.
6. Farries, T C; Lachmann, P J & Harrison, R A (1988) *Biochem. J.* 253:667–75.
7. Forty, J; Hasan, R; Cary, N; White, D J & Wallwork, J (1992) *Transplant. Proc.* 24:488–9.
8. Fritzinger, D. C. et al. (1992) *J. Immunol*. 149:3554–3562.
9. Harrison, R. A. & Lachmann, P. J. (1980) *Mol. Immunol*. 17:9–20.
10. Kalli, K. R., Hsu, P. & Fearon, D. T. (1994) *Springer Semin. Immunopathol*. 15:417–431.
11. Kinoshita, T; Takata, Y; Kozono, H; Takeda, J; Hong, K S & Inoue, K (1988) *J. Iumunol*. 141:3895–901.
12. McNearney, T A; Odell, C; Holers, V M; Spear, P G; Atkinson, J P (1987) *J. Exp. Med*. 166:1525–35.
13. Nicol, P. A. E. & Lachmann, P. J. (1973) *Immunol*. 24:259–275.
14. Pangburn, M K & Muller-Eberhard, H J (1964) *Springer Semin. Immunopathol*. 7:163–92.
15. Rother, K. & Till, G. O. (eds) (1988) "*The complement System*" (Springer-Verlag Berlin Heidelberg, Germany).
16. Van den Berg, C. W., Aerts, P. C. & Van Dijk, H. (1991) *J. Immunol. Methods* 136:287–294.
17. Vogel, C W; Smith, C A & Muller-Eberhard, H J (1984) *J. Immunol.* 133:3235–41.
18. Weisman, H F et al. (1990) *Science* 249:146–51.
19. Wu, R. (ed.) (1993) *Methods Enzymol*. 217: ch.s 12–14 (Academic Press, San Diego, U.S.A.).
20. Botto, M, Fang, K. Y., So, A. K., Koch, C. & Walport, M. J. (1990) *J. Exp. Med*. 172:1011–7
21. Sambrook, J., Fritsch, E. F. & Maniatis, T. (1989) "*Molecular Cloning. A Laboratory Manual*" second edition (Cold Spring Harbor Laboratory Press).
22. Fishelson, Z. (1991) *Mol. Immunol*. 28:545–52.
23. Taniguchi-Sidle, A & Isenman, D. E. (1993) *Mol. Immunol*. 30:54.
24. Lambris, J. D., Avila, D., Becherer, J. D. & Muller, Eberhard, H. J. (1988) *J. Biol. Chem*. 263:2147–50.
25. Taniguchi-Sidle, A. and Isenman, D. E. (1992) *J. Biol. Chem*. 267:635–643.
26. Hofer, B. and Kuhlein, B. (1993) *Methods Enzymol*. 217:173–189.
27. Morinaga, Y., Franceschini, T., Inouye, S. and Inouye, M. (1984) *Bio-technology* 2:636–639.
28. Harrison, R. A. and Lachmann, P. J. (1986) "*Handbook of Experimental Immunology*" (eds Weir, Herzenberg, Blackwell and Herzenberg; Blackwell, Oxford) 4th ed.,
29. Kotwal, G., J., and Moss, B., *Nature* (1988) 335 (6186): 176–8.

What is claimed is:

1. An isolated DNA sequence encoding a modified human C3 protein of SEQ ID No: 22, wherein the modification consists of one or more mutations selected from the group consisting of:

E992S, D993A, D996S, A997Q, E 998S, R999G, L1000M, K1001N, H1002I, V1005H, Q1152R, E1153K, K1155F, R954E, the double mutant R954Q+ E955G, and REA1591-3TN stop.

* * * * *

SEQUENCE LISTING

<160> NUMBER OF SEQ ID NOS: 35

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence: oligodeoxynucleotide PL-ATC-3

<400> SEQUENCE: 1
tagggagacc ggaagcttgc cctctccctc tgtccctctg t                          41

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: mutagenic oligodeoxynucleotide QRI1

<400> SEQUENCE: 2

```
caactgccca gccaaagctc caagatcacc                                            30
```

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:
      oligodeoxynucleotide QRI2

<400> SEQUENCE: 3

```
gccagcctcc tgcaatcaga agagaccaag                                            30
```

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence:
      oligodeoxynucleotide AFL4149

<400> SEQUENCE: 4

```
taataaattc gaccttaagg tcaccataaa ac                                         32
```

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:  antisense
      oligodeoxynucleotide QRI1n

<400> SEQUENCE: 5

```
ggtgatcttg gagctttggc tgggcagttg                                            30
```

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:
      antisense oligodeoxynucleotide
      QRI2n

<400> SEQUENCE: 6

```
cttggtctct tctgattgca ggaggctggc                                            30
```

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: antisense
      oligonucleotide AFL4149n

<400> SEQUENCE: 7

```
gttttatggt gaccttaagg tcgaatttat ta                                         32
```

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: mutagenic
      primer

<400> SEQUENCE: 8

-continued

```
caactgccca gckrsagctc caagatcacc                                      30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 9
caccaggaac tgaatctaga tgtgtccctc                                      30

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 10
gttttatggt gaccttaagg tcgaatttat ta                                   32

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: mutagenic
      oligonucleotide

<400> SEQUENCE: 11
agtaacctgg gttcgggcat cattgcagga tcggcatcg tttcc                      45

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: mutagenic
      oligonucleotide

<400> SEQUENCE: 12
tggtgttgac caatacatct ccgactatca gctggacaa                            39

<210> SEQ ID NO 13
<211> LENGTH: 44
<212> TYPE: DNA
<213> ORGANISM: Homo sapiens

<400> SEQUENCE: 13
tgggtgcccc aaccatcatc atcatcatca ttgaccacac cccc                      44

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: mutagenic
      primer

<400> SEQUENCE: 14
ccagatgaca agtgctgccg tcagccagtc agggctgaag cacc                      44

<210> SEQ ID NO 15
<211> LENGTH: 20
<212> TYPE: DNA
```

```
<213> ORGANISM: Artificial Sequence
<220> FEATURE:
<223> OTHER INFORMATION: Description of Artificial Sequence: primer

<400> SEQUENCE: 15
tgtcatcgtg ccgctaaaga                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: mutagenic
      primer

<400> SEQUENCE: 16
tgtcatcgtg ccgctaaaga                                               20

<210> SEQ ID NO 17
<211> LENGTH: 35
<212> TYPE: DNA
<213> ORGANISM: Homo sapiens

<400> SEQUENCE: 17
aacggctgaa catattaatt cataccccct cgggc                              35

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: mutagenic
      primer

<400> SEQUENCE: 18
atctcgctgc gcaaggcttt cgatatttgc gag                                33

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: mutagenic
      primer

<400> SEQUENCE: 19
gaacgcctgg gcgaagaagg agtgcag                                       27

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: mutagenic
      primer

<400> SEQUENCE: 20
aacgcctggg ccaaggagga gtgcagaa                                      28

<210> SEQ ID NO 21
<211> LENGTH: 14
<212> TYPE: PRT
<213> ORGANISM: Homo sapiens

<400> SEQUENCE: 21

Glu Asp Ala Val Asp Ala Glu Arg Leu Lys His Leu Ile Val
```

-continued

<210> SEQ ID NO 22
<211> LENGTH: 1663
<212> TYPE: PRT
<213> ORGANISM: Homo sapiens

<400> SEQUENCE: 22

```
Met Gly Pro Thr Ser Gly Pro Ser Leu Leu Leu Leu Thr His
  1               5                  10                  15

Leu Pro Leu Ala Leu Gly Ser Pro Met Tyr Ser Ile Ile Thr Pro Asn
             20                  25                  30

Ile Leu Arg Leu Glu Ser Glu Glu Thr Met Val Leu Glu Ala His Asp
         35                  40                  45

Ala Gln Gly Asp Val Pro Val Thr Val Thr Val His Asp Phe Pro Gly
     50                  55                  60

Lys Lys Leu Val Leu Ser Ser Glu Lys Thr Val Leu Thr Pro Ala Thr
 65                  70                  75                  80

Asn His Met Gly Asn Val Thr Phe Thr Ile Pro Ala Asn Arg Glu Phe
                 85                  90                  95

Lys Ser Glu Lys Gly Arg Asn Lys Phe Val Thr Val Gln Ala Thr Phe
            100                 105                 110

Gly Thr Gln Val Val Glu Lys Val Val Leu Val Ser Leu Gln Ser Gly
        115                 120                 125

Tyr Leu Phe Ile Gln Thr Asp Lys Thr Ile Tyr Thr Pro Gly Ser Thr
    130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
                165                 170                 175

Gln Asp Ser Leu Ser Ser Gln Asn Gln Leu Gly Val Leu Pro Leu Ser
            180                 185                 190

Trp Asp Ile Pro Glu Leu Val Asn Met Gly Gln Trp Lys Ile Arg Ala
        195                 200                 205

Tyr Tyr Glu Asn Ser Pro Gln Gln Val Phe Ser Thr Glu Phe Glu Val
    210                 215                 220

Lys Glu Tyr Val Leu Pro Ser Phe Glu Val Ile Val Glu Pro Thr Glu
225                 230                 235                 240

Lys Phe Tyr Tyr Ile Tyr Asn Glu Lys Gly Leu Glu Val Thr Ile Thr
                245                 250                 255

Ala Arg Phe Leu Tyr Gly Lys Lys Val Glu Gly Thr Ala Phe Val Ile
            260                 265                 270

Phe Gly Ile Gln Asp Gly Glu Gln Arg Ile Ser Leu Pro Glu Ser Leu
        275                 280                 285

Lys Arg Ile Pro Ile Glu Asp Gly Ser Gly Glu Val Val Leu Ser Arg
    290                 295                 300

Lys Val Leu Leu Asp Gly Val Gln Asn Pro Arg Ala Glu Asp Leu Val
305                 310                 315                 320

Gly Lys Ser Leu Tyr Val Ser Ala Thr Val Ile Leu His Ser Gly Ser
                325                 330                 335

Asp Met Val Gln Ala Glu Arg Ser Gly Ile Pro Ile Val Thr Ser Pro
            340                 345                 350

Tyr Gln Ile His Phe Thr Lys Thr Pro Lys Tyr Phe Lys Pro Gly Met
        355                 360                 365
```

```
Pro Phe Asp Leu Met Val Phe Val Thr Asn Pro Asp Gly Ser Pro Ala
    370                 375                 380

Tyr Arg Val Pro Val Ala Val Gln Gly Glu Asp Thr Val Gln Ser Leu
385                 390                 395                 400

Thr Gln Gly Asp Gly Val Ala Lys Leu Ser Ile Asn Thr His Pro Ser
            405                 410                 415

Gln Lys Pro Leu Ser Ile Thr Val Arg Thr Lys Lys Gln Glu Leu Ser
            420                 425                 430

Glu Ala Glu Gln Ala Thr Arg Thr Met Gln Ala Leu Pro Tyr Ser Thr
        435                 440                 445

Val Gly Asn Ser Asn Asn Tyr Leu His Leu Ser Val Leu Arg Thr Glu
    450                 455                 460

Leu Arg Pro Gly Glu Thr Leu Asn Val Asn Phe Leu Leu Arg Met Asp
465                 470                 475                 480

Arg Ala His Glu Ala Lys Ile Arg Tyr Tyr Thr Tyr Leu Ile Met Asn
            485                 490                 495

Lys Gly Arg Leu Leu Lys Ala Gly Arg Gln Val Arg Glu Pro Gly Gln
            500                 505                 510

Asp Leu Val Val Leu Pro Leu Ser Ile Thr Thr Asp Phe Ile Pro Ser
        515                 520                 525

Phe Arg Leu Val Ala Tyr Tyr Thr Leu Ile Gly Ala Ser Gly Gln Arg
530                 535                 540

Glu Val Val Ala Asp Ser Val Trp Val Asp Val Lys Asp Ser Cys Val
545                 550                 555                 560

Gly Ser Leu Val Val Lys Ser Gly Gln Ser Glu Asp Arg Gln Pro Val
            565                 570                 575

Pro Gly Gln Gln Met Thr Leu Lys Ile Glu Gly Asp His Gly Ala Arg
            580                 585                 590

Val Val Leu Val Ala Val Asp Lys Gly Val Phe Val Leu Asn Lys Lys
        595                 600                 605

Asn Lys Leu Thr Gln Ser Lys Ile Trp Asp Val Val Glu Lys Ala Asp
    610                 615                 620

Ile Gly Cys Thr Pro Gly Ser Gly Lys Asp Tyr Ala Gly Val Phe Ser
625                 630                 635                 640

Asp Ala Gly Leu Thr Phe Thr Ser Ser Ser Gly Gln Gln Thr Ala Gln
            645                 650                 655

Arg Ala Glu Leu Gln Cys Pro Gln Pro Ala Ala Arg Arg Arg Arg Ser
            660                 665                 670

Val Gln Leu Thr Glu Lys Arg Met Asp Lys Val Gly Lys Tyr Pro Lys
        675                 680                 685

Glu Leu Arg Lys Cys Cys Glu Asp Gly Met Arg Glu Asn Pro Met Arg
    690                 695                 700

Phe Ser Cys Gln Arg Arg Thr Arg Phe Ile Ser Leu Gly Glu Ala Cys
705                 710                 715                 720

Lys Lys Val Phe Leu Asp Cys Cys Asn Tyr Ile Thr Glu Leu Arg Arg
            725                 730                 735

Gln His Ala Arg Ala Ser His Leu Gly Leu Ala Arg Ser Asn Leu Asp
            740                 745                 750

Glu Asp Ile Ile Ala Glu Asn Ile Val Ser Arg Ser Glu Phe Pro
        755                 760                 765

Glu Ser Trp Leu Trp Asn Val Glu Asp Leu Lys Glu Pro Pro Lys Asn
    770                 775                 780

Gly Ile Ser Thr Lys Leu Met Asn Ile Phe Leu Lys Asp Ser Ile Thr
```

```
                785                 790                 795                 800
Thr Trp Glu Ile Leu Ala Val Ser Met Ser Asp Lys Lys Gly Ile Cys
                805                 810                 815
Val Ala Asp Pro Phe Glu Val Thr Val Met Gln Asp Phe Phe Ile Asp
            820                 825                 830
Leu Arg Leu Pro Tyr Ser Val Arg Asn Glu Gln Val Glu Ile Arg
            835                 840                 845
Ala Val Leu Tyr Asn Tyr Arg Gln Asn Gln Glu Leu Lys Val Arg Val
    850                 855                 860
Glu Leu Leu His Asn Pro Ala Phe Cys Ser Leu Ala Thr Thr Lys Arg
865                 870                 875                 880
Arg His Gln Gln Thr Ile Thr Ile Pro Pro Lys Ser Ser Leu Ser Val
                885                 890                 895
Pro Tyr Val Ile Val Pro Leu Lys Thr Gly Leu Gln Glu Val Glu Val
            900                 905                 910
Lys Ala Ala Val Tyr His His Phe Ile Ser Asp Gly Val Arg Lys Ser
            915                 920                 925
Leu Lys Val Val Pro Glu Gly Ile Arg Met Asn Lys Thr Val Ala Val
    930                 935                 940
Arg Thr Leu Asp Pro Glu Arg Leu Gly Arg Glu Gly Val Gln Lys Glu
945                 950                 955                 960
Asp Ile Pro Pro Ala Asp Leu Ser Asp Gln Val Pro Asp Thr Glu Ser
                965                 970                 975
Glu Thr Arg Ile Leu Leu Gln Gly Thr Pro Val Ala Gln Met Thr Glu
            980                 985                 990
Asp Ala Val Asp Ala Glu Arg Leu Lys His Leu Ile Val Thr Pro Ser
            995                 1000                1005
Gly Cys Gly Glu Gln Asn Met Ile Gly Met Thr Pro Thr Val Ile Ala
    1010                1015                1020
Val His Tyr Leu Asp Glu Thr Glu Gln Trp Glu Lys Phe Gly Leu Glu
1025                1030                1035                1040
Lys Arg Gln Gly Ala Leu Glu Leu Ile Lys Lys Gly Tyr Thr Gln Gln
            1045                1050                1055
Leu Ala Phe Arg Gln Pro Ser Ser Ala Phe Ala Ala Phe Val Lys Arg
            1060                1065                1070
Ala Pro Ser Thr Trp Leu Thr Ala Tyr Val Val Lys Val Phe Ser Leu
    1075                1080                1085
Ala Val Asn Leu Ile Ala Ile Asp Ser Gln Val Leu Cys Gly Ala Val
    1090                1095                1100
Lys Trp Leu Ile Leu Glu Lys Gln Lys Pro Asp Gly Val Phe Gln Glu
1105                1110                1115                1120
Asp Ala Pro Val Ile His Gln Glu Met Ile Gly Gly Leu Arg Asn Asn
            1125                1130                1135
Asn Glu Lys Asp Met Ala Leu Thr Ala Phe Val Leu Ile Ser Leu Gln
            1140                1145                1150
Glu Ala Lys Asp Ile Cys Glu Glu Gln Val Asn Ser Leu Pro Gly Ser
    1155                1160                1165
Ile Thr Lys Ala Gly Asp Phe Leu Glu Ala Asn Tyr Met Asn Leu Gln
    1170                1175                1180
Arg Ser Tyr Thr Val Ala Ile Ala Gly Tyr Ala Leu Ala Gln Met Gly
1185                1190                1195                1200
Arg Leu Lys Gly Pro Leu Leu Asn Lys Phe Leu Thr Thr Ala Lys Asp
            1205                1210                1215
```

-continued

```
Lys Asn Arg Trp Glu Asp Pro Gly Lys Gln Leu Tyr Asn Val Glu Ala
        1220                1225                1230
Thr Ser Tyr Ala Leu Leu Ala Leu Leu Gln Leu Lys Asp Phe Asp Phe
    1235                1240                1245
Val Pro Pro Val Val Arg Trp Leu Asn Glu Gln Arg Tyr Tyr Gly Gly
1250                1255                1260
Gly Tyr Gly Ser Thr Gln Ala Thr Phe Met Val Phe Gln Ala Leu Ala
1265                1270                1275                1280
Gln Tyr Gln Lys Asp Ala Pro Asp His Gln Glu Leu Asn Leu Asp Val
                1285                1290                1295
Ser Leu Gln Leu Pro Ser Arg Ser Ser Lys Ile Thr His Arg Ile His
            1300                1305                1310
Trp Glu Ser Ala Ser Leu Leu Arg Ser Glu Glu Thr Lys Glu Asn Glu
        1315                1320                1325
Gly Phe Thr Val Thr Ala Glu Gly Lys Gly Gln Gly Thr Leu Ser Val
    1330                1335                1340
Val Thr Met Tyr His Ala Lys Ala Lys Asp Gln Leu Thr Cys Asn Lys
1345                1350                1355                1360
Phe Asp Leu Lys Val Thr Ile Lys Pro Ala Pro Glu Thr Glu Lys Arg
                1365                1370                1375
Pro Gln Asp Ala Lys Asn Thr Met Ile Leu Glu Ile Cys Thr Arg Tyr
            1380                1385                1390
Arg Gly Asp Gln Asp Ala Thr Met Ser Ile Leu Asp Ile Ser Met Met
        1395                1400                1405
Thr Gly Phe Ala Pro Asp Thr Asp Asp Leu Lys Gln Leu Ala Asn Gly
    1410                1415                1420
Val Asp Arg Tyr Ile Ser Lys Tyr Glu Leu Asp Lys Ala Phe Ser Asp
1425                1430                1435                1440
Arg Asn Thr Leu Ile Ile Tyr Leu Asp Lys Val Ser His Ser Glu Asp
                1445                1450                1455
Asp Cys Leu Ala Phe Lys Val His Gln Tyr Phe Asn Val Glu Leu Ile
            1460                1465                1470
Gln Pro Gly Ala Val Lys Val Tyr Ala Tyr Tyr Asn Leu Glu Glu Ser
        1475                1480                1485
Cys Thr Arg Phe Tyr His Pro Glu Lys Glu Asp Gly Lys Leu Asn Lys
    1490                1495                1500
Leu Cys Arg Asp Glu Leu Cys Arg Cys Ala Glu Glu Asn Cys Phe Ile
1505                1510                1515                1520
Gln Lys Ser Asp Asp Lys Val Thr Leu Glu Glu Arg Leu Asp Lys Ala
                1525                1530                1535
Cys Glu Pro Gly Val Asp Tyr Val Tyr Lys Thr Arg Leu Val Lys Val
            1540                1545                1550
Gln Leu Ser Asn Asp Phe Asp Glu Tyr Ile Met Ala Ile Glu Gln Thr
        1555                1560                1565
Ile Lys Ser Gly Ser Asp Glu Val Gln Val Gly Gln Gln Arg Thr Phe
    1570                1575                1580
Ile Ser Pro Ile Lys Cys Arg Glu Ala Leu Lys Leu Glu Glu Lys Lys
1585                1590                1595                1600
His Tyr Leu Met Trp Gly Leu Ser Ser Asp Phe Trp Gly Glu Lys Pro
                1605                1610                1615
Asn Leu Ser Tyr Ile Ile Gly Lys Asp Thr Trp Val Glu His Trp Pro
            1620                1625                1630
```

-continued

Glu Glu Asp Glu Cys Gln Asp Glu Glu Asn Gln Lys Gln Cys Gln Asp
     1635                1640                1645

Leu Gly Ala Phe Thr Glu Ser Met Val Val Phe Gly Cys Pro Asn
    1650                1655                1660

<210> SEQ ID NO 23
<211> LENGTH: 5067
<212> TYPE: DNA
<213> ORGANISM: Homo sapiens

<400> SEQUENCE: 23

| | | | | | |
|---|---|---|---|---|---|
| ctcctcccca | tcctctccct | ctgtccctct | gtccctctga | ccctgcactg | tcccagcacc | 60 |
| atgggaccca | cctcaggtcc | cagcctgctg | ctcctgctac | taacccacct | cccctggct | 120 |
| ctggggagtc | ccatgtactc | tatcatcacc | cccaacatct | gcggctgga | gagcgaggag | 180 |
| accatggtgc | tggaggccca | cgacgcgcaa | ggggatgttc | cagtcactgt | tactgtccac | 240 |
| gacttcccag | gcaaaaaact | agtgctgtcc | agtgagaaga | ctgtgctgac | ccctgccacc | 300 |
| aaccacatgg | gcaacgtcac | cttcacgatc | ccagccaaca | gggagttcaa | gtcagaaaag | 360 |
| gggcgcaaca | agttcgtgac | cgtgcaggcc | accttcggga | cccaagtggt | ggagaaggtg | 420 |
| gtgctggtca | gcctgcagag | cgggtacctc | ttcatccaga | cagacaagac | catctacacc | 480 |
| cctggctcca | cagttctcta | tcggatcttc | accgtcaacc | acaagctgct | acccgtgggc | 540 |
| cggacggtca | tggtcaacat | tgagaaccgc | gaaggcatcc | cggtcaagca | ggactccttg | 600 |
| tcttctcaga | accagcttgg | cgtcttgccc | ttgtcttggg | acattccgga | actcgtcaac | 660 |
| atgggccagt | ggaagatccg | agcctactat | gaaaactcac | acagcaggt | cttctccact | 720 |
| gagtttgagg | tgaaggagta | cgtgctgccc | agtttcgagg | tcatagtgga | gcctacagag | 780 |
| aaattctact | acatctataa | cgagaagggc | ctggaggtca | ccatcaccgc | caggttcctc | 840 |
| tacgggaaga | agtggaggg | aactgccttt | gtcatcttcg | ggatccagga | tggcgaacag | 900 |
| aggatttccc | tgcctgaatc | cctcaagcgc | attccgattg | aggatggctc | ggggagttt | 960 |
| gtgctgagcc | ggaaggtact | gctggacggg | gtgcagaacc | ccgagcaga | agacctggtg | 1020 |
| gggaagtctt | tgtacgtgtc | tgccaccgtc | atcttgcact | caggcagtga | catggtgcag | 1080 |
| gcagagcgca | gcgggatccc | catcgtgacc | tctccctacc | agatccactt | caccaagaca | 1140 |
| cccaagtact | tcaaaccagg | aatgcccttt | gacctcatgg | tgttcgtgac | gaaccctgat | 1200 |
| ggctctccag | cctaccgagt | ccccgtggca | gtccagggcg | aggacactgt | gcagtctcta | 1260 |
| acccaggag | atggcgtggc | caaactcagc | atcaacacac | ccccagcca | gagcccttg | 1320 |
| agcatcacgg | tgcgcacgaa | gaagcaggag | ctctcggagg | cagagcaggc | taccaggacc | 1380 |
| atgcaggctc | tgcccctacag | caccgtgggc | aactccaaca | attacctgca | tctctcagtg | 1440 |
| ctacgtacag | agctcagacc | cggggagacc | ctcaacgtca | acttcctcct | gcgaatggac | 1500 |
| cgcgcccacg | aggccaagat | ccgctactac | acctacctga | tcatgaacaa | gggcaggctg | 1560 |
| ttgaaggcgg | gacgccaggt | gcgagagccc | ggccaggacc | tggtggtgct | gcccctgtcc | 1620 |
| atcaccaccg | acttcatccc | ttccttccgc | ctggtggcgt | actacacgct | gatcggtgcc | 1680 |
| agcggccaga | gggaggtggt | ggccgactcc | gtgtgggtgg | acgtcaagga | ctcctgcgtg | 1740 |
| ggctcgctgg | tggtaaaaag | cggccagtca | gaagaccggc | agcctgtacc | tgggcagcag | 1800 |
| atgaccctga | agatagaggg | tgaccacggg | gcccgggtgg | tactggtggc | cgtggacaag | 1860 |
| ggcgtgttcg | tgctgaataa | gaagaacaaa | ctgacgcaga | gtaagatctg | ggacgtggtg | 1920 |
| gagaaggcag | acatcggctg | cacccccggc | agtgggaagg | attacgccgg | tgtcttctcc | 1980 |

-continued

```
gacgcagggc tgaccttcac gagcagcagt ggccagcaga ccgcccagag ggcagaactt    2040
cagtgcccgc agccagccgc ccgccgacgc cgttccgtgc agctcacgga gaagcgaatg    2100
gacaaagtcg gcaagtaccc caaggagctg cgcaagtgct gcgaggacgg catgcgggag    2160
aaccccatga ggttctcgtg ccagcgccgg acccgtttca tctccctggg cgaggcgtgc    2220
aagaaggtct tcctggactg ctgcaactac atcacagagc tgcggcggca gcacgcgcgg    2280
gccagccacc tgggcctggc caggagtaac ctggatgagg acatcattgc agaagagaac    2340
atcgtttccc gaagtgagtt cccagagagc tggctgtgga cgttgagga cttgaaagag     2400 ccaccgaaaa atggaatctc tacgaagctc atgaatatat ttttgaaaga ctccatcacc    2460
acgtgggaga ttctggctgt gagcatgtcg gacaagaaag ggatctgtgt ggcagacccc    2520
ttcgaggtca cagtaatgca ggacttcttc atcgacctgc ggctacccta ctctgttgtt    2580
cgaaacgagc aggtggaaat ccgagccgtt ctctacaatt accggcagaa ccaagagctc    2640
aaggtgaggg tggaactact ccacaatcca gccttctgca gcctggccac caccaagagg    2700
cgtcaccagc agaccataac catccccccc aagtcctcgt tgtccgttcc atatgtcatc    2760
gtgccgctaa agaccggcct gcaggaagtg gaagtcaagg ctgctgtcta ccatcatttc    2820
atcagtgacg tgtcaggaa gtccctgaag gtcgtgccgg aaggaatcag aatgaacaaa     2880
actgtggctg ttcgcaccct ggatccagaa cgcctgggcc gtgaaggagt gcagaaagag    2940
gacatcccac ctgcagacct cagtgaccaa gtcccggaca ccgagtctga gaccagaatt    3000
ctcctgcaag ggaccccagt ggcccagatg acagaggatg ccgtcgacgc ggaacggctg    3060
aagcacctca ttgtgacccc ctcgggctgc ggggaacaga acatgatcgg catgacgccc    3120
acggtcatcg ctgtgcatta cctggatgaa acggagcagt gggagaagtt cggcctagag    3180
aagcggcagg gggccttgga gctcatcaag aaggggtaca cccagcagct ggccttcaga    3240
caacccagct ctgcctttgc ggccttcgtg aaacgggcac ccagcacctg gctgaccgcc    3300
tacgtggtca aggtcttctc tctggctgtc aacctcatcg ccatcgactc ccaagtcctc    3360
tgcggggctg ttaaatggct gatcctggag aagcagaagc ccgacggggt cttccaggag    3420
gatgcgcccg tgatacacca agaaatgatt ggtggattac ggaacaacaa cgagaaagac    3480
atggccctca cggcctttgt tctcatctcg ctgcaggagg ctaaagatat ttgcgaggag    3540
caggtcaaca gcctgccagg cagcatcact aaagcaggag acttccttga agccaactac    3600
atgaacctac agagatccta cactgtggcc attgctggct atgctctggc ccagatgggc    3660
aggctgaagg ggcctcttct taacaaattt ctgaccacag ccaaagataa gaaccgctgg    3720
gaggaccctg gtaagcagct ctacaacgtg gaggccacat cctatgccct cttggcccta    3780
ctgcagctaa aagactttga ctttgtgcct cccgtcgtgc gttggctcaa tgaacagaga    3840
tactacggtg gtggctatgg ctctacccag gccaccttca tggtgttcca agccttggct    3900
caataccaaa aggacgcccc tgaccaccag gaactgaacc ttgatgtgtc cctccaactg    3960
cccagccgca gctccaagat cacccaccgt atccactggg aatctgccag cctcctgcga    4020
tcagaagaga ccaaggaaaa tgagggtttc acagtcacag ctgaaggaaa aggccaaggc    4080
accttgtcgg tggtgacaat gtaccatgct aaggccaaag atcaactcac ctgtaataaa    4140
ttcgacctca aggtcaccat aaaaccagca ccggaaacag aaaagaggcc tcaggatgcc    4200
aagaacacta tgatccttga gatctgtacc aggtaccggg gagaccagga tgccactatg    4260
tctatattgg acatatccat gatgactggc tttgctccag acacagatga cctgaagcag    4320
```

```
ctggccaatg gtgttgacag atacatctcc aagtatgagc tggacaaagc cttctccgat    4380
aggaacaccc tcatcatcta cctggacaag gtctcacact ctgaggatga ctgtctagct    4440
ttcaaagttc accaatactt taatgtagag cttatccagc ctggagcagt caaggtctac    4500
gcctattaca acctggagga aagctgtacc cggttctacc atccggaaaa ggaggatgga    4560
aagctgaaca agctctgccg tgatgaactg tgccgctgtg ctgaggagaa ttgcttcata    4620
caaaagtcgg atgacaaggt caccctggaa gaacggctgg acaaggcctg tgagccagga    4680
gtggactatg tgtacaagac ccgactggtc aaggttcagc tgtccaatga ctttgacgag    4740
tacatcatgg ccattgagca gaccatcaag tcaggctcgg atgaggtgca ggttggacag    4800
cagcgcacgt tcatcagccc catcaagtgc agagaagccc tgaagctgga ggagaagaaa    4860
cactacctca tgtggggtct ctcctccgat ttctggggag agaagcccaa cctcagctac    4920
atcatcggga aggacacttg ggtggagcac tggcctgagg aggacgaatg ccaagacgaa    4980
gagaaccaga aacaatgcca ggacctcggc gccttcaccg agagcatggt tgtctttggg    5040
tgccccaact gaccacaccc ccattcc                                        5067
```

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: mutagenic
      oligodeoxynucleotide QRI1

<400> SEQUENCE: 24
cttcatggtg ttccaagcct                                                20

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: nucleotide
      insertion

<400> SEQUENCE: 25
catcatcatc atcatcat                                                  18

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: amino acid
      insertion

<400> SEQUENCE: 26

His His His His His His
 1               5

<210> SEQ ID NO 27
<211> LENGTH: 8
<212> TYPE: PRT
<213> ORGANISM: Homo sapiens

<400> SEQUENCE: 27

Leu Ser Ser Asp Phe Trp Gly Glu
 1               5

<210> SEQ ID NO 28

```
<211> LENGTH: 6
<212> TYPE: PRT
<213> ORGANISM: Artificial Sequence
<220> FEATURE:
<223> OTHER INFORMATION: Description of Artificial Sequence: replacement
      sequence

<400> SEQUENCE: 28

Lys Glu Ala Leu Gln Ile
  1               5

<210> SEQ ID NO 29
<211> LENGTH: 5
<212> TYPE: PRT
<213> ORGANISM: Homo sapiens

<400> SEQUENCE: 29

Ile Ile Gly Lys Asp
  1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: replacement
      sequence

<400> SEQUENCE: 30

Arg Tyr Ile Tyr Pro Leu Asp Ser Leu
  1               5

<210> SEQ ID NO 31
<211> LENGTH: 4
<212> TYPE: PRT
<213> ORGANISM: Homo sapiens

<400> SEQUENCE: 31

Glu Glu Asp Glu
  1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: replacement
      sequence

<400> SEQUENCE: 32

Arg Asp Thr Thr
  1

<210> SEQ ID NO 33
<211> LENGTH: 8
<212> TYPE: PRT
<213> ORGANISM: Homo sapiens

<400> SEQUENCE: 33

Gln Asp Glu Glu Asn Gln Lys Gln
  1               5

<210> SEQ ID NO 34
<211> LENGTH: 8
<212> TYPE: PRT
<213> ORGANISM: Artificial Sequence
<220> FEATURE:
```

```
<223> OTHER INFORMATION: Description of Artificial Sequence: replacement
      sequence

<400> SEQUENCE: 34

Arg Ser Thr Arg Gln Arg Ala Ala
 1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: replacement
      sequence

<400> SEQUENCE: 35

Ala Phe Leu Ala Asn
 1               5
```